(12) United States Patent
Brockschmidt, Jr. et al.

(10) Patent No.: US 12,288,951 B2
(45) Date of Patent: Apr. 29, 2025

(54) SYSTEMS AND METHODS FOR MAINTAINING ELECTRICAL CONTACT IN RELATION TO AN ULTRAVIOLET LAMP

(71) Applicant: THE BOEING COMPANY, Chicago, IL (US)

(72) Inventors: Arthur Edward Brockschmidt, Jr., Renton, WA (US); Kevin S. Callahan, Everett, WA (US); Jamie J. Childress, Mercer Island, WA (US)

(73) Assignee: The Boeing Company, Chicago, IL (US)

( * ) Notice: Subject to any disclaimer, the term of this patent is extended or adjusted under 35 U.S.C. 154(b) by 937 days.

(21) Appl. No.: 17/342,602

(22) Filed: Jun. 9, 2021

(65) Prior Publication Data

US 2021/0399440 A1 Dec. 23, 2021

Related U.S. Application Data

(60) Provisional application No. 63/040,109, filed on Jun. 17, 2020.

(51) Int. Cl.
| | |
|---|---|
| *H01R 4/14* | (2006.01) |
| *A61L 2/10* | (2006.01) |
| *A61L 2/26* | (2006.01) |
| *H01R 4/28* | (2006.01) |
| *B64F 5/30* | (2017.01) |
| *H01J 61/12* | (2006.01) |

(52) U.S. Cl.
CPC .............. *H01R 4/14* (2013.01); *A61L 2/10* (2013.01); *A61L 2/26* (2013.01); *H01R 4/28* (2013.01); *A61L 2202/11* (2013.01); *A61L 2202/16* (2013.01); *A61L 2202/25* (2013.01); *B64F 5/30* (2017.01); *H01J 61/12* (2013.01)

(58) Field of Classification Search
CPC ..... H01R 4/14; H01R 4/28; H01J 1/12; A61L 2/10; A61L 2/26; A61L 2202/11; A61L 2202/16; A61L 2202/25
USPC ........................................................ 439/799
See application file for complete search history.

(56) References Cited

U.S. PATENT DOCUMENTS 4,080,024 A * 3/1978 Kroon .................... H01R 4/646
439/98
4,237,174 A * 12/1980 Lagardere ........... B29C 66/1122
174/DIG. 8
(Continued)

FOREIGN PATENT DOCUMENTS

| CN | 101772821 | 7/2010 |
|---|---|---|
| CN | 102792389 | 11/2012 |

(Continued)

OTHER PUBLICATIONS

Extended European Search Report for EP 21180076.8-1004, dated Nov. 16, 2021.

(Continued)

*Primary Examiner* — Harshad C Patel
(74) *Attorney, Agent, or Firm* — Joseph M. Butscher; The Small Patent LAw Group LLC

(57) ABSTRACT

A system for connecting an ultraviolet (UV) lamp with an electrical coupling includes a braid attachment coupled to the UV lamp, and one or both of a compressive wrap secured around at least a portion of the braid attachment, or a clamp secured around at least a portion of the braid attachment.

21 Claims, 17 Drawing Sheets

(56) References Cited

U.S. PATENT DOCUMENTS

| | | | | |
|---|---|---|---|---|
| 4,790,765 | A * | 12/1988 | Ehrenfels | H01R 13/33 439/98 |
| 5,028,742 | A * | 7/1991 | Redman | H02G 15/068 439/98 |
| 5,556,309 | A * | 9/1996 | Sharpe | H01R 11/282 439/759 |
| 5,755,597 | A * | 5/1998 | Panis | H01R 13/59 439/471 |
| 5,911,595 | A * | 6/1999 | Orr, Jr. | H01R 13/58 439/471 |
| 6,164,987 | A * | 12/2000 | Mirabella | H05K 9/0018 439/639 |
| 6,202,300 | B1 * | 3/2001 | Yuzwalk | H01R 4/643 439/813 |
| 7,052,331 | B2 * | 5/2006 | Maxwell | H01R 11/285 24/274 R |
| 7,112,094 | B2 * | 9/2006 | Reilly | H01R 13/5804 439/607.51 |
| 7,258,304 | B2 * | 8/2007 | Miener | H01R 4/646 248/62 |
| 7,762,685 | B1 | 7/2010 | Beucler | |
| 10,224,668 | B2 * | 3/2019 | Benton | H01R 13/5205 |
| 10,457,317 | B2 * | 10/2019 | Takagi | B62D 5/0409 |
| 2004/0171306 | A1 * | 9/2004 | Reilly | H01R 13/5804 439/607.51 |
| 2010/0253207 | A1 * | 10/2010 | Joulaud | H01J 61/305 313/484 |

FOREIGN PATENT DOCUMENTS

| | | |
|---|---|---|
| CN | 203423269 | 2/2014 |
| CN | 110352540 | 10/2019 |
| JP | H11 265689 | 9/1999 |
| JP | 2016-143610 | 8/2016 |
| JP | 2010-525509 | 7/2017 |
| WO | WO 2005/098904 | 10/2005 |

OTHER PUBLICATIONS

U.S. Appl. No. 16/987,493, filed Aug. 7, 2020.
"Honeywell UV Treatment System," https://aerospace.honeywell.com/en/learn/products/cabin/uv-cabin-system.
CN Office Action for CN App. No. 202110673988.8, dated Dec. 25, 2024.

* cited by examiner

SYSTEMS AND METHODS FOR MAINTAINING ELECTRICAL CONTACT IN RELATION TO AN ULTRAVIOLET LAMP

RELATED APPLICATIONS

This application relates to and claims priority benefits from U.S. Provisional Patent Application No. 63/040,109, entitled "Systems and Methods for Maintaining Electrical Contact in Relation to an Ultraviolet Lamp," filed Jun. 17, 2020, which is hereby incorporated by reference in its entirety.

FIELD OF THE DISCLOSURE

Embodiments of the present disclosure generally relate to sanitizing systems, such as may be used to sanitize structures and areas within vehicles, such as commercial aircraft, and more particularly to systems and methods for maintaining electrical contact in relation to ultraviolet lamps of sanitizing systems.

BACKGROUND OF THE DISCLOSURE

Vehicles such as commercial aircraft are used to transport passengers between various locations. Systems are currently being developed to disinfect or otherwise sanitize surfaces within aircraft, for example, that use ultraviolet (UV) light.

In order to sanitize a surface of a structure, a known UV light sterilization method emits a broad spectrum UVC light onto the structure. However, UVC light typically takes a significant amount of time (for example, three minutes) to kill various microbes. Further, various microbes may not be vulnerable to UVC light. That is, such microbes may be able to withstand exposure to UVC light.

Also, certain types of microbes may develop a resistance to UVC light. For example, while UVC light may initially kill certain types of microbes, with continued exposure to UVC light over time, the particular species of microbe may develop a resistance to UVC light and able to withstand UVC light exposure.

Additionally, direct exposure of certain types of UV light may pose risk to humans. For example, certain known UV systems emit UV light having a wavelength of 254 nm, which may pose a risk to humans. As such, certain known UV light disinfection systems and methods are operated in the absence of individuals. For example, a UV light disinfection system within a lavatory may be operated when no individual is within the lavatory, and deactivated when an individual is present within the lavatory.

Further, certain UV light sanitizing systems include excimer lamps. Electrical connections to excimer lamps may be less than reliable due to generated heat. For example, a 222 nm UV lamp may have a low temperature solder joint that attaches an electrical braid to the lamp, which may result in failure of the connection at the high operating temperatures of the UV lamp. The generated heat may break a grid line in the braid attachment. Further, tape that is disposed over the braid attachment may also inadvertently pull the grid line off when the tape is removed. Further, the resulting arcing may adversely affect neighboring grid lines, which may lead to the lamp being disconnected from the electrical coupling.

SUMMARY OF THE DISCLOSURE

A need exists for a system and a method for maintaining a reliable connection between a lamp of a sanitizing system and an electrical coupling.

With that need in mind, certain embodiments of the present disclosure provide a system for connecting an ultraviolet (UV) lamp with an electrical coupling. The system includes a braid attachment of the UV lamp, and a compressive wrap secured around at least a portion of the braid attachment. In at least one embodiment, the compressive wrap is formed of fiberglass.

The system may also include a conductive layer secured to the at least a portion of the braid attachment. The compressive wrap may be secured around at least a portion of the conductive layer. The conductive layer may include a foil.

In at least one embodiment, the compressive wrap includes ends tied together in a knot. In at least one embodiment, an epoxy bonds the knot. The knot may be separated from the at least a portion of the braid attachment by wrapped layers of the compressive wrap.

In at least one embodiment, the system also includes a clamp secured around one or both of the at least a portion of the braid attachment or at least a portion of the compressive wrap. The clamp may be formed of a plastic.

In at least one embodiment, the clamp includes expanded ends connected together by a recessed connecting beam. The recessed connecting beam may inwardly curve toward the UV lamp. A thickness of the clamp may vary around a perimeter.

Certain embodiments of the present disclosure provide a method for connecting an ultraviolet (UV) lamp with an electrical coupling. The method includes coupling a braid attachment to a UV lamp, and securing a compressive wrap around at least a portion of the braid attachment.

In at least one embodiment, the method also includes securing a clamp around one or both of the at least a portion of the braid attachment or at least a portion of the compressive wrap.

Certain embodiments of the present disclosure provide a system for connecting an ultraviolet (UV) lamp with an electrical coupling. The system includes a braid attachment of the UV lamp, and a clamp secured around at least a portion of the braid attachment.

Certain embodiments of the present disclosure provide a method for connecting an ultraviolet (UV) lamp with an electrical coupling. The method includes coupling a braid attachment to a UV lamp, and securing a clamp around at least a portion of the braid attachment.

DETAILED DESCRIPTION OF THE DISCLOSURE

Figure 1:
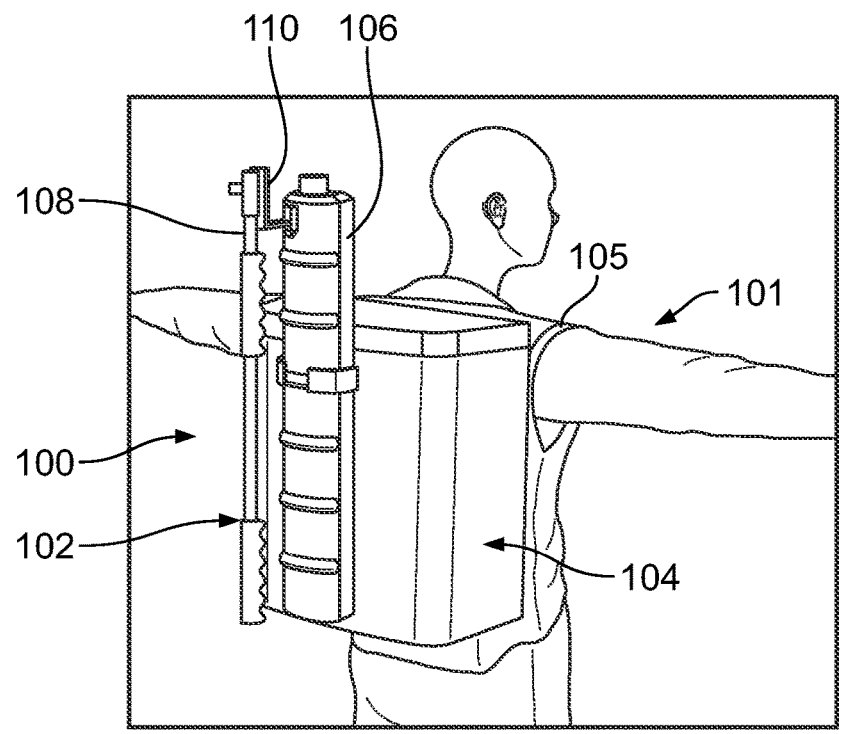
FIG. 1 illustrates a perspective view of a portable sanitizing system worn by an individual, according to an embodiment of the present disclosure.

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular condition can include additional elements not having that condition.

Certain embodiments of the present disclosure provide a sanitizing system and method that includes an ultraviolet (UV) lamp (such as an excimer lamp) that emits UV light in a far UV light spectrum, such as at a wavelength of 222 nm, which neutralizes (such as kills) microbes (for example, viruses and bacteria), while posing no risk to humans. The UV lamp may be used within an internal cabin to decontaminate and kill pathogens. Embodiments of the present disclosure provide safer and more effective sanitation as compared to certain known UV systems. The UV lamp may be used in a portable sanitizing system or a fixed sanitizing system. For example, operating the UV lamp to emit sanitizing UV light having a wavelength of 222 nm may be used with a portable system or a fixed system.

Certain embodiments of the present disclosure provide a method to maintain an electrical connection and contact in relation to an ultraviolet (UV) lamp, such as a 222 nm excimer lamp. In at least one embodiment, the method includes applying a thin conductive layer (such as formed of copper of aluminum) at a compression point where the electrical connection contacts the UV lamp. The method also includes compressing the conductive layer and electrical connection to the compression point with a mechanical restraining device such as tape or a clamp. The tape and/or clamp is formed of materials that maintain structural and thermal capabilities at a temperature of at least 200 degrees C., for example.

In at least one embodiment, the method includes first applying a conductive layer to provide a greater area of electrical contact and spread heat to prevent a thermal hotspot. Next, the method includes applying a mechanical restraining device to secure the electrical braid and conductive layer together.

In at least one embodiment, the conductive layer is a thin material capable of conforming to the curved surface on the lamp, and is of a similar length as the lamp grid. The tape could be made of materials such as polyimide (Kapton), PEEK, Teflon, or Fiberglass, and is wrapped around the compression point to secure the conductive layer and electrical braid. The clamp may be formed of a thermoplastic material, and may have a C or U shape, with a hook on an open side to attach the open ends together to provide additional clamping force. The clamp is placed on the compression point to mechanically secure the conductive layer and electrical braid.

In at least one embodiment, embodiments of the present disclosure provide an application of copper foil to prevent detachment of a conductive adhesive on high temperature excimer lamp. Further, embodiments of the present disclosure may be used to repair such connections.

In at least one embodiment, a constraint is used to secure a connection interface of a UV lamp. The constraint can be used with or without a conductive layer, such as a copper strip or a copper tape that is configured to spread current and provide a heat sink. Examples of the constraint include a clamp, a tape, a fiberglass wrap, a non-conductive fiber wrap, a pressure clip, or other the like. In at least one embodiment, the constraint includes two or more of the clamp, the tape, the fiberglass wrap, the non-conductive fiber wrap, the pressure clip, and/or the like.

Certain embodiments of the present disclosure provide a method for maintaining electrical contact in relation to a UV lamp (such as a 222 nm UV lamp). The method includes applying a thin electrically conductive layer form of materials such as copper or aluminum at a compression point where the electrical connection contacts the UV lamp, and compressing the conductive layer and the electrical connection to the compression point with a mechanical restraining device or constraint, such as tape, a clamp, a clip, a fiberglass wrap, or a continuous band. The mechanical restraining device or constraint is formed of one or more materials that are capable of maintaining structural and thermal capabilities at a temperature of at least 200 degrees C., for example.

In at least one embodiment, the mechanical restraining device or constraint is a fiberglass tension wrap that is wrapped around the compression point to secure a conductive layer to an electrical braid. The fiberglass tension wrap is tied around the conductive layer, and the resulting knot is bonded together using an adhesive such as epoxy or a resin thermoset. A clamp may be formed of a thermoplastic material and may have a C or U shape with a hook, latch, or spring on an open side to attach the open ends together to provide additional clamping force. In at least one embodiment, the clamp may be of a continuous design, such as a band, with varying thickness around the perimeter for desired stiffness properties. A curved beam may be used to allow for a high preload and low spring rate to mitigate differences in thermal expansion between the UV lamp and the clip.

FIG. 1 illustrates a perspective view of a portable sanitizing system 100 worn by an individual 101, according to an embodiment of the present disclosure. The portable sanitizing system 100 includes a wand assembly 102 coupled to a backpack assembly 104 that is removably secured to the individual through a harness 105. The wand assembly 102 includes a sanitizing head 106 coupled to a handle 108. In at least one embodiment, the sanitizing head 106 is moveably coupled to the handle 108 through a coupler 110.

As shown in FIG. 1, the wand assembly 102 is in a stowed position. In the stowed position, the wand assembly 102 is removably secured to a portion of the backpack assembly 104, such as through one or more tracks, clips, latches, belts, ties, and/or the like.

Figure 2:
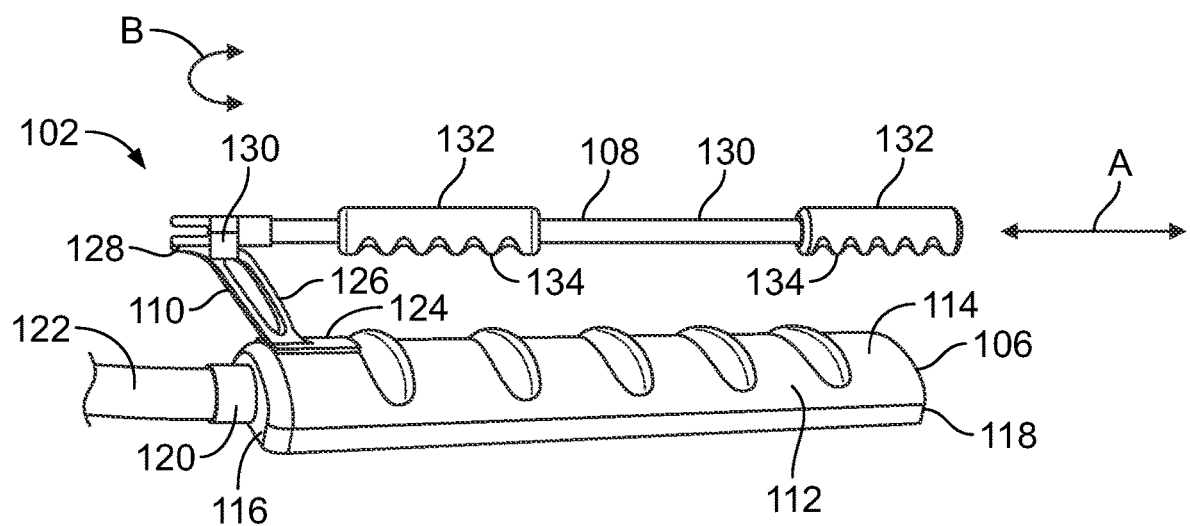
FIG. 2 illustrates a perspective lateral top view of a wand assembly, according to an embodiment of the present disclosure.

FIG. 2 illustrates a perspective lateral top view of the wand assembly 102, according to an embodiment of the present disclosure. The sanitizing head 106 couples to the handle 108 through the coupler 110. The sanitizing head 106 includes a shroud 112 having an outer cover 114 that extends from a proximal end 116 to a distal end 118. As described herein, the shroud 112 contains a UV lamp, such as a 222 nm excimer lamp.

A port 120 extends from the proximal end 116. The port 120 couples to a hose 122, which, in turn, couples to the backpack assembly 104 (shown in FIG. 1). The hose 122 contains electrical cords, cables, wiring, or the like that couples a power source or supply (such as one or more batteries) within the backpack assembly 104 (shown in FIG. 1) to a UV lamp 140 within the shroud 112. Optionally, the electrical cords, cables, wiring, or the like may be outside of the hose 122. The hose 122 also contains an air delivery line, such as an air tube) that fluidly couples an internal chamber of the shroud 112 to an air blower, vacuum generator, air filters, and/or the like within the backpack assembly 104.

The coupler 110 is secured to the outer cover 114 of the shroud 112, such as proximate to the proximal end 116. The coupler 110 may include a securing beam 124 secured to the outer cover 114, such as through one or more fasteners, adhesives, and/or the like. An extension beam 126 outwardly extends from the securing beam 124, thereby spacing the handle 108 from the shroud 112. A bearing assembly 128 extends from the extension beam 126 opposite from the securing beam 124. The bearing assembly 128 includes one or more bearings, tracks, and/or the like, which allow the handle 108 to linearly translate relative to the coupler 110 in the directions of arrows A, and/or pivot about a pivot axle in the directions of arc B. Optionally, the securing beam 124 may include a bearing assembly that allows the sanitizing head 106 to translate in the directions of arrows A, and/or rotate (for example, swivel) in the directions of arc B in addition to, or in place of, the handle 108 being coupled to the bearing assembly 128 (for example, the handle 108 may be fixed to the coupler 110).

In at least one embodiment, the handle 108 includes a rod, pole, beam, or the like 130, which may be longer than the shroud 112. Optionally, the rod 130 may be shorter than the shroud 112. One or more grips 132 are secured to the rod 130. The grips 132 are configured to be grasped and held by an individual. The grips 132 may include ergonomic tactile features 134.

Figure 3:
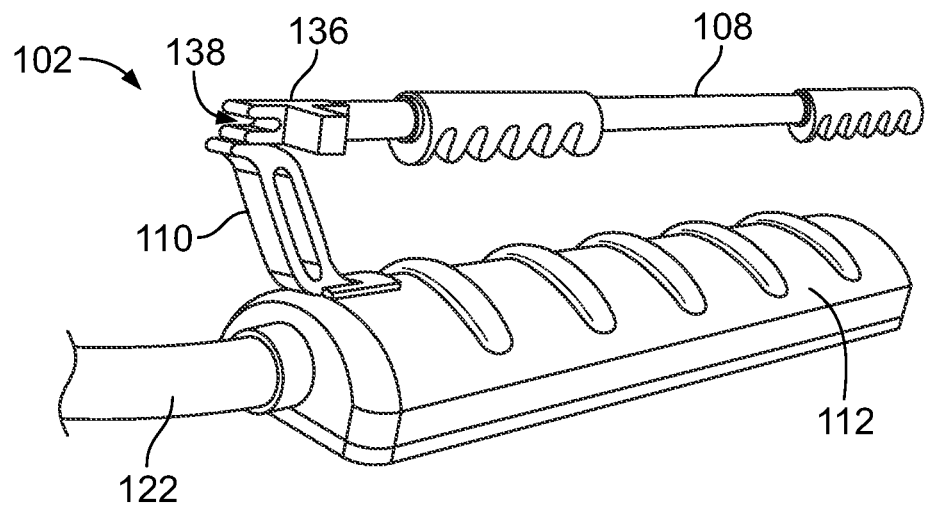
FIG. 3 illustrates a perspective rear view of the wand assembly of FIG. 2.
Figure 4:
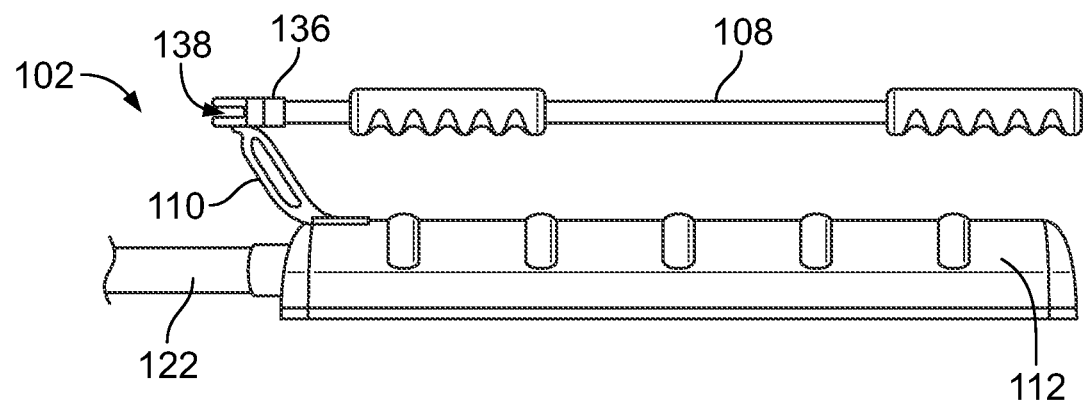
FIG. 4 illustrates a perspective lateral view of the wand assembly of FIG. 2.

FIG. 3 illustrates a perspective rear view of the wand assembly 102 of FIG. 2. FIG. 4 illustrates a perspective lateral view of the wand assembly 102 of FIG. 2. Referring to FIGS. 3 and 4, the handle 108 may pivotally couple to the coupler 110 through a bearing 136 having a pivot axle 138 that pivotally couples the handle 108 to the coupler 110. The handle 108 may further be configured to linearly translate into and out of the bearing 136. For example, the handle 108 may be configured to telescope in and out. Optionally, or alternatively, in at least one embodiment, the handle 108 may include a telescoping body that allows the handle 108 to outwardly extend and inwardly recede.

Figure 5:
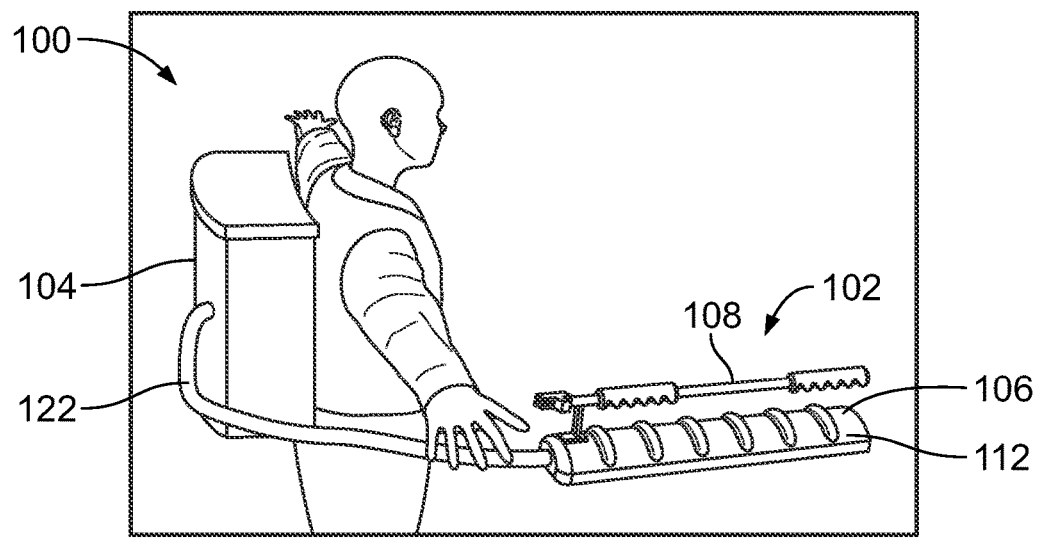
FIG. 5 illustrates a perspective view of the portable sanitizing system in a compact deployed position, according to an embodiment of the present disclosure.

FIG. 5 illustrates a perspective view of the portable sanitizing system 100 in a compact deployed position, according to an embodiment of the present disclosure. The wand assembly 102 is removed from the backpack assembly 104 (as shown in FIG. 1) into the compact deployed position, as shown in FIG. 5. The hose 122 connects the wand assembly 102 to the backpack assembly 104. In the compact deployed position, the sanitizing head 106 is fully retracted in relation to the handle 108.

Figure 6:
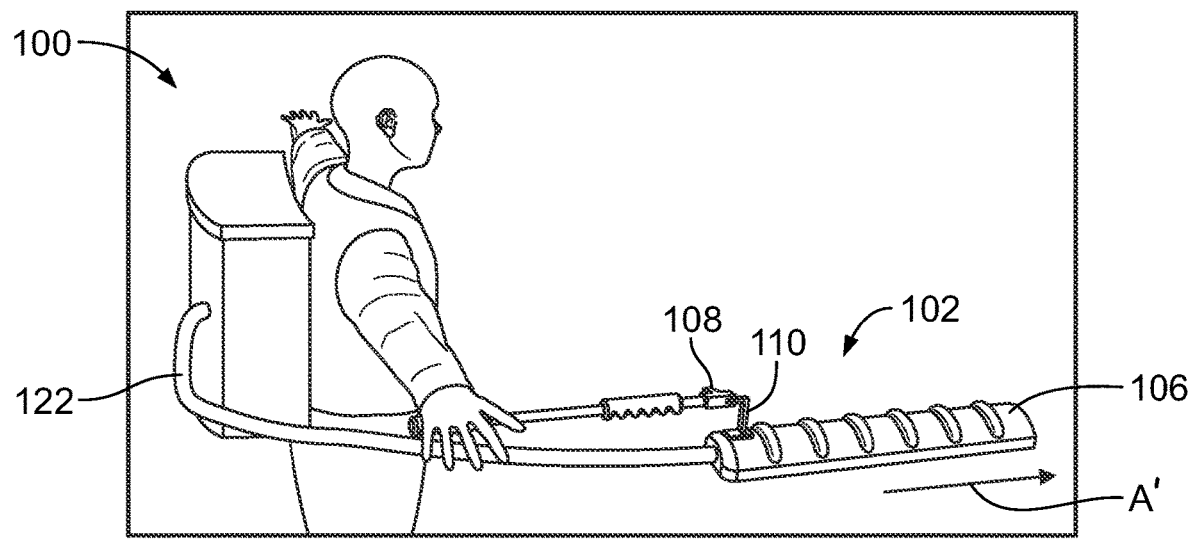
FIG. 6 illustrates a perspective view of the portable sanitizing system having a sanitizing head in an extended position, according to an embodiment of the present disclosure.

FIG. 6 illustrates a perspective view of the portable sanitizing system 100 having the sanitizing head 106 in an extended position, according to an embodiment of the present disclosure. In order to extend the sanitizing head 106 relative to the handle 108, the sanitizing head 106 is outwardly slid relative to the handle 108 in the direction of arrow A' (or the handle 108 is rearwardly slid relative to the sanitizing head 106). As noted, the sanitizing head 106 is able to linearly translate in the direction of arrow A' relative to the handle 108 via the coupler 110. The outward extension of the sanitizing head 106, as shown in FIG. 6, allows for the portable sanitizing system 100 to easily reach distant areas. Alternatively, the sanitizing head 106 may not linearly translate relative to the handle 108.

Figure 7:
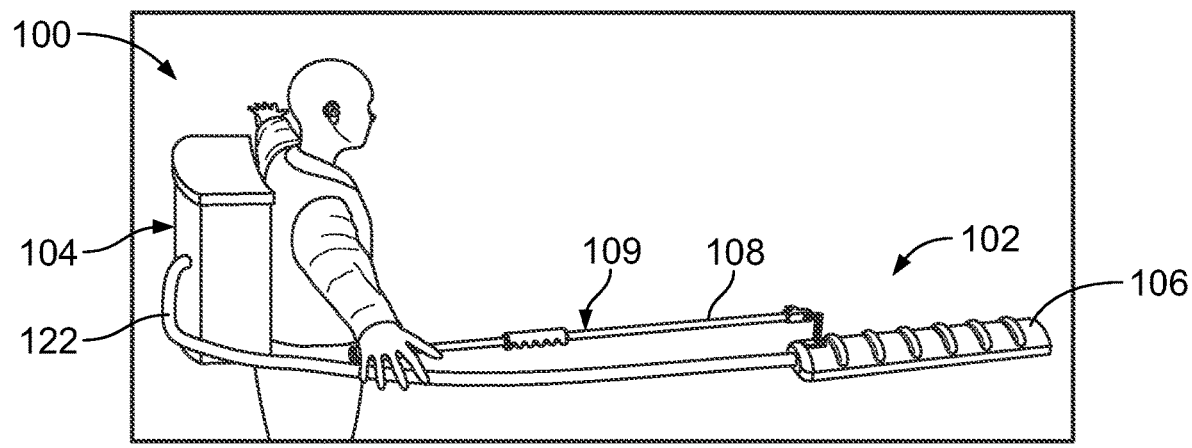
FIG. 7 illustrates a perspective view of the portable sanitizing system having the sanitizing head in an extended position and a handle in an extended position, according to an embodiment of the present disclosure.

FIG. 7 illustrates a perspective view of the portable sanitizing system 100 having the sanitizing head 106 in an extended position and the handle 108 in an extended position, according to an embodiment of the present disclosure. To reach even further, the handle 108 may be configured to linearly translate, such as through a telescoping portion, to allow the sanitizing head 106 to reach further outwardly. Alternatively, the handle 108 may not be configured to extend and retract.

In at least one embodiment, the handle 108 may include a lock 109. The lock 109 is configured to be selectively operated to secure the handle 108 into a desired extended (or retracted) position.

Figure 8:
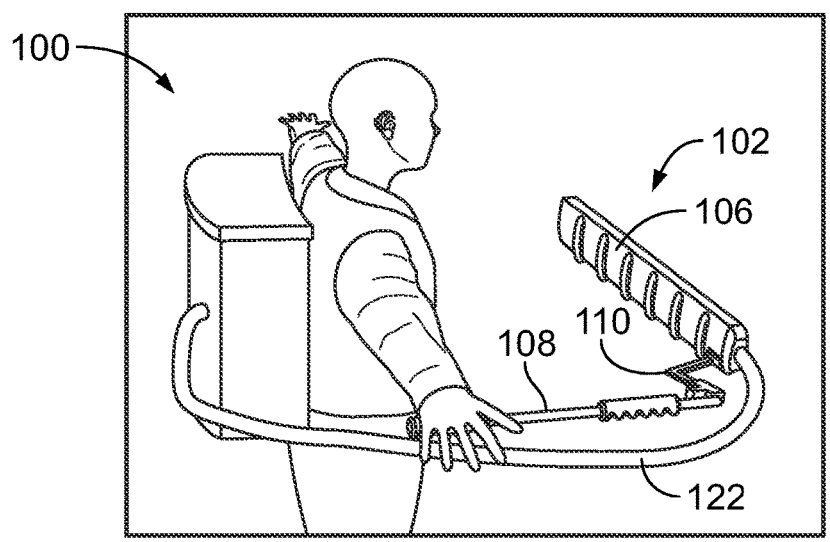
FIG. 8 illustrates a perspective view of the portable sanitizing system having the sanitizing head rotated in relation to the handle, according to an embodiment of the present disclosure.

FIG. 8 illustrates a perspective view of the portable sanitizing system 100 having the sanitizing head 106 rotated in relation to the handle 108, according to an embodiment of the present disclosure. As noted, the sanitizing head 106 is configured to rotate relative to the handle 108 via the coupler 110. Rotating the sanitizing head 106 relative to the handle 108 allows the sanitizing head 106 to be moved to a desired position, and sweep or otherwise reach into areas that would otherwise be difficult to reach if the sanitizing head 106 was rigidly fixed to the handle 108. Alternatively, the sanitizing head 106 may not be rotatable relative to the handle 108. Appendix A illustrates different positions of the wand assembly 102.

Figure 9:
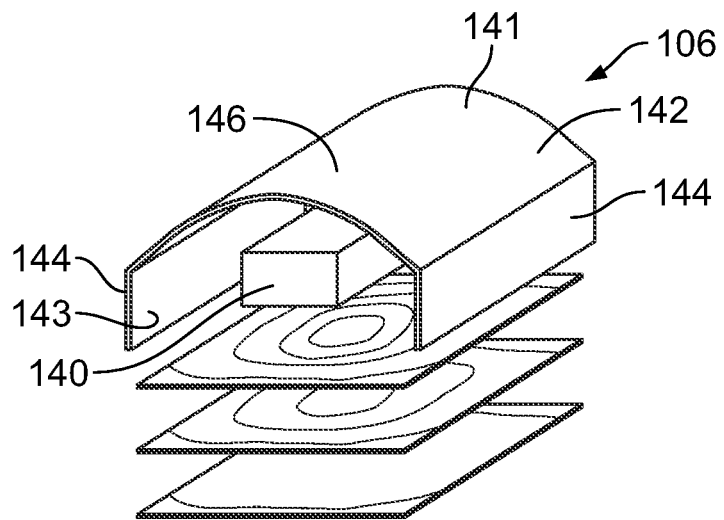
FIG. 9 illustrates a perspective end view of a UV lamp and a reflector of the sanitizing head, according to an embodiment of the present disclosure.

FIG. 9 illustrates a perspective end view of a UV lamp 140 and a reflector 142 of the sanitizing head 106, according to an embodiment of the present disclosure. The UV lamp 140 and the reflector 142 are secured within the shroud 112 (shown in FIG. 2, for example) of the sanitizing head 106. In at least one embodiment, the reflector 142 is secured to an underside 141 of the shroud 112, such as through one or more adhesives. As another example, the reflector 142 is an integral part of the shroud 112. For example, the reflector 142 may be or otherwise provide the underside 141 of the shroud 112. The reflector 142 provides a reflective surface 143 (such as formed of Teflon, a mirrored surface, and/or the like) that is configured to outwardly reflect UV light emitted by the UV lamp 140. In at least one example, shroud 112 may be or include a shell formed of fiberglass, and the reflector 142 may be formed of Teflon that provides a 98% reflectivity.

The reflector 142 may extend along an entire length of the underside 141 of the shroud 112. Optionally, the reflector 142 may extend along less than an entire length of the underside 141 of the shroud 112.

The UV lamp 140 may extend along an entire length (or along substantially the entire length, such as between the ends 116 and 118). The UV lamp 140 is secured to the reflector 142 and/or the shroud 112 through one or more brackets, for example. The UV lamp 140 includes one or more UV light emitters, such as one more bulbs, light emitting elements (such as light emitting diodes), and/or the like. In at least one embodiment, the UV lamp 140 is configured to emit UV light in the far UV spectrum, such as at a wavelength between 200 nm-230 nm. In at least one embodiment, the UV lamp 140 is configured to emit UV light having a wavelength of 222 nm. For example, the UV lamp 140 may be or include a 300 W bulb that is configured to emit UV light having a wavelength of 222 nm.

As shown, the reflector 142 includes flat, upright side walls 144 connected together through an upper curved wall 146. The upper curved wall 146 may be bowed outwardly away from the UV lamp 140. For example, the upper curved wall 146 may have a parabolic cross-section and/or profile.

It has been found that the straight, linear side walls 144 provide desired reflection and/or focusing of UV light emitted from the UV lamp 140 toward and onto a desired location. Alternatively, the side walls 144 may not be linear and flat.

Figure 10:
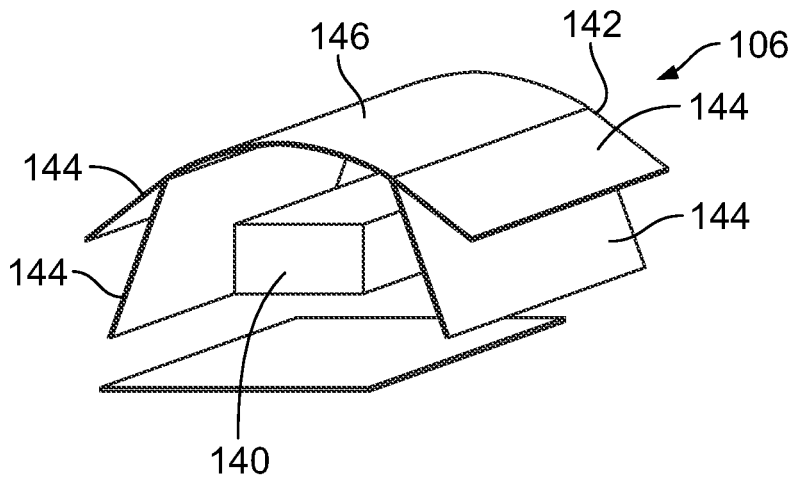
FIG. 10 illustrates a perspective end view of a UV lamp and a reflector of the sanitizing head, according to an embodiment of the present disclosure.

FIG. 10 illustrates a perspective end view of the UV lamp 140 and a reflector 142 of the sanitizing head, according to an embodiment of the present disclosure. The reflector 142 shown in FIG. 10 is similar to the reflector 142 shown in FIG. 9, except that the side walls 144 may outwardly cant from the upper curved wall 146.

Figure 11:
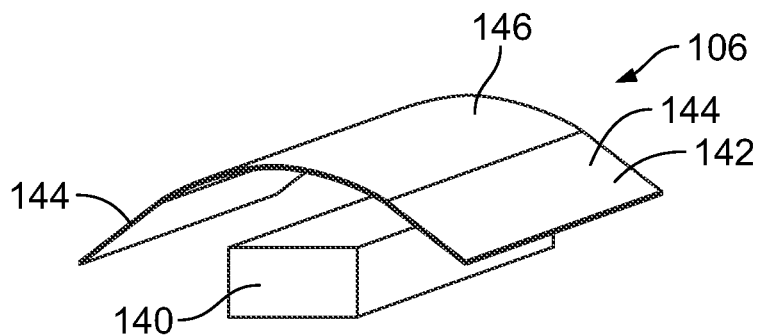
FIG. 11 illustrates a perspective end view of a UV lamp and a reflector of the sanitizing head, according to an embodiment of the present disclosure.

FIG. 11 illustrates a perspective end view of the UV lamp 140 and the reflector 142 of the sanitizing head, according to an embodiment of the present disclosure. In this embodiment, the side walls 144 may be curved according to the curvature of the upper curved wall 146.

Figure 12:
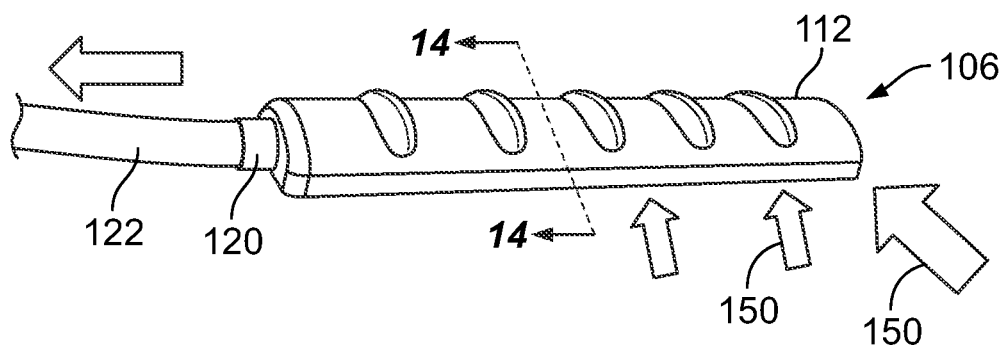
FIG. 12 illustrates a perspective top view of the sanitizing head.
Figure 13:
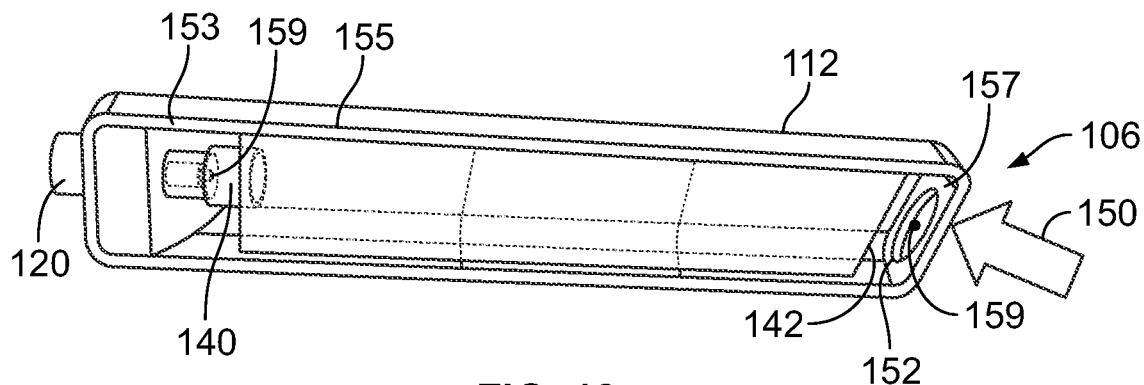
FIG. 13 illustrates a perspective bottom view of the sanitizing head.
Figure 14:
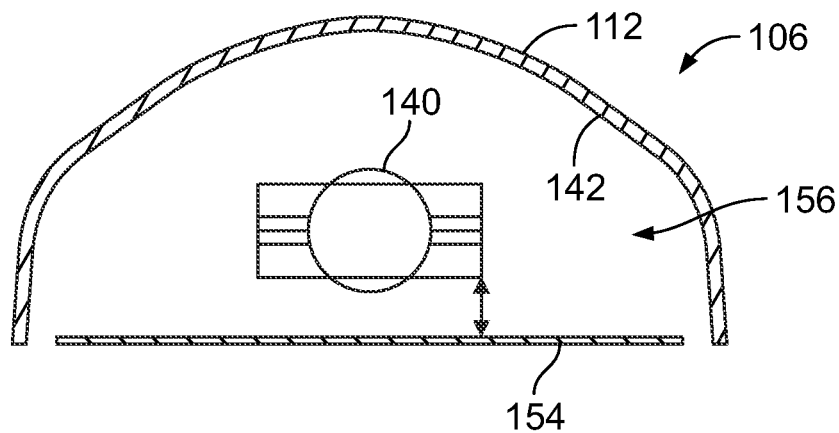
FIG. 14 illustrates an axial cross-sectional view of the sanitizing head through line 14-14 of FIG. 12.

FIG. 12 illustrates a perspective top view of the sanitizing head 106. FIG. 13 illustrates a perspective bottom view of the sanitizing head 106. FIG. 14 illustrates an axial cross-sectional view of the sanitizing head 106 through line 14-14 of FIG. 12. Referring to FIGS. 12-14, air 150 is configured to be drawn into the sanitizing head 106 through one or more openings 152 (or simply an open chamber) of the shroud 112. The air 150 is drawn into the sanitizing head 106, such as via a vacuum generator within the backpack assembly 104 (shown in FIG. 1). The air 150 is drawn into the shroud 112, and cools the UV lamp 140 as it passes over and around the UV lamp 140. The air 150 passes into the port 120 and into the hose 122, such as within an air tube within the hose 122. The air 150 not only cools the UV lamp 140, but also removes ozone, which may be generated by operation of the UV lamp 140, within the shroud 112. The air 150 may be drawn to an air filter, such as an activated carbon filter, within the backpack assembly 104.

In at least one embodiment, the portable sanitizing system 100 may also include an alternative ozone mitigation system. As an example, the ozone mitigation system may be disposed in the shroud 112 or another portion of the system, and may include an inert gas bath, or a face inert gas system, such as in U.S. Pat. No. 10,232,954.

Referring to FIG. 13, in particular, a bumper 153 may be secured to an exposed lower circumferential edge 155 of the shroud 112. The bumper 153 may be formed of a resilient material, such as rubber, another elastomeric material, open or closed cell foam, and/or the like. The bumper 153 protects the sanitizing head 106 from damage in case the sanitizing head 106 inadvertently contacts a surface. The bumper 153 also protects the surface from damage.

The openings 152 may be spaced around the lower surface of the shroud 112 such that they do not provide a direct view of the UV lamp 140. For example, the openings 152 may be positioned underneath portions that are spaced apart from the UV lamp 140.

Referring to FIG. 14, in particular, the sanitizing head 106 may include a cover plate 154 below the UV lamp 140. The cover plate 154 may be formed of glass, for example, and may be configured to filter UV light emitted by the UV lamp 140. The UV lamp 140 may be secured within an interior chamber 156 defined between the reflector 142 and the cover plate 154. In at least one embodiment, the cover plate 154 is or otherwise includes a far UV band pass filter. For example, the cover plate 154 may be a 222 nm band pass filter that filters UV light emitted by the UV lamp 140 to a 222 nm wavelength. As such, UV light that is emitted from the sanitizing head 106 may be emitted at a wavelength of 222 nm.

Referring to FIGS. 13 and 14, a rim 157 (such as a 0.020" thick Titanium rim) may connect the cover plate 154 to the shroud 112. The rim 157 may distribute impact loads therethrough and/or therearound.

In at least one embodiment, ranging light emitting diodes (LEDs) 159 may be disposed proximate to ends of the UV lamp 140. The ranging LEDs 159 may be used to determine a desired range to a structure that is to be sanitized, for example. In at least one embodiment, the ranging LEDs 159 may be disposed on or within the rim 157 and/or the cover plate 154.

Figure 15:
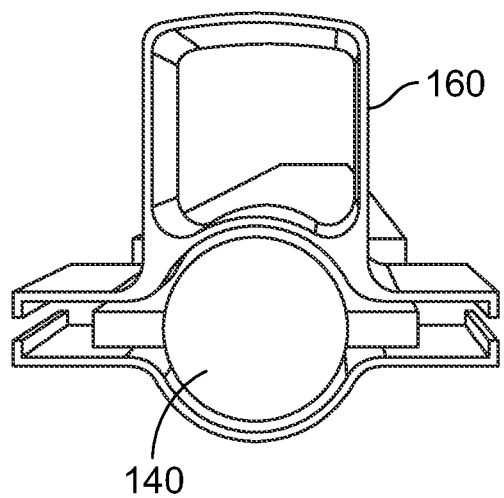
FIG. 15 illustrates a perspective end view of the UV lamp secured to a mounting bracket, according to an embodiment of the present disclosure.

FIG. 15 illustrates a perspective end view of the UV lamp 140 secured to a mounting bracket or clamp 160, according to an embodiment of the present disclosure. Each end of the UV lamp 140 may be coupled to mounting bracket or clamp 160, which secures the UV lamp 140 to the shroud 112 (shown in FIGS. 12-14). A buffer, such as a thin (for example, 0.040") sheet of silicon may be disposed between the end of the UV lamp 140 and the bracket 160. Optionally, the UV lamp 140 may be secured to the shroud 112 through brackets or clamps that differ in size and shape than shown. As another example, the UV lamp 140 may be secured to the shroud 112 through adhesives, fasteners, and/or the like.

Figure 16:
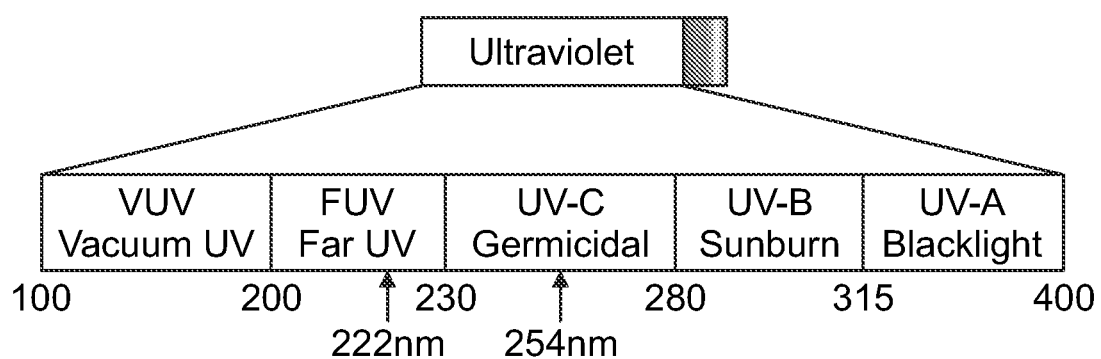
FIG. 16 illustrates an ultraviolet light spectrum.

FIG. 16 illustrates an ultraviolet light spectrum. Referring to FIGS. 1-16, in at least one embodiment, the sanitizing head 106 is configured to emit sanitizing UV light (through operation of the UV lamp 140) within a far UV spectrum, such as between 200 nm to 230 nm. In at least one embodiment, the sanitizing head 106 emits sanitizing UV light having a wavelength of 222 nm.

Embodiments of the present disclosure provide systems and methods for maintaining a reliable electrical connection in relation to a UV lamp, such as a 222 nm UV lamp. Optionally, the UV lamp can be operated at different wavelengths, such as 200 nm or 230 nm. In at least one other embodiment, the UV lamp can be operated within the UV-C spectrum.

Optionally, the UV light may be at various other wavelengths. For example, the UV light may be within the far UV spectrum, such as between 220-230 nm. As another example, the UV light may be within the UVC spectrum, such as between 230-280 nm. As an example, the UV light may be emitted at a wavelength of 254 nm.

In at least one embodiment, the UV lamp is the UV lamp 140 within a portable sanitizing system, such as shown and described with respect to FIGS. 1-15. Optionally, embodiments of the present disclosure may be used with fixed sanitizing systems. For example, embodiments of the present disclosure may be used with UV lamps that are fixed within a structure, such as UV lamps that are fixed to a ceiling, a wall, a floor, or the like.

Figure 17:
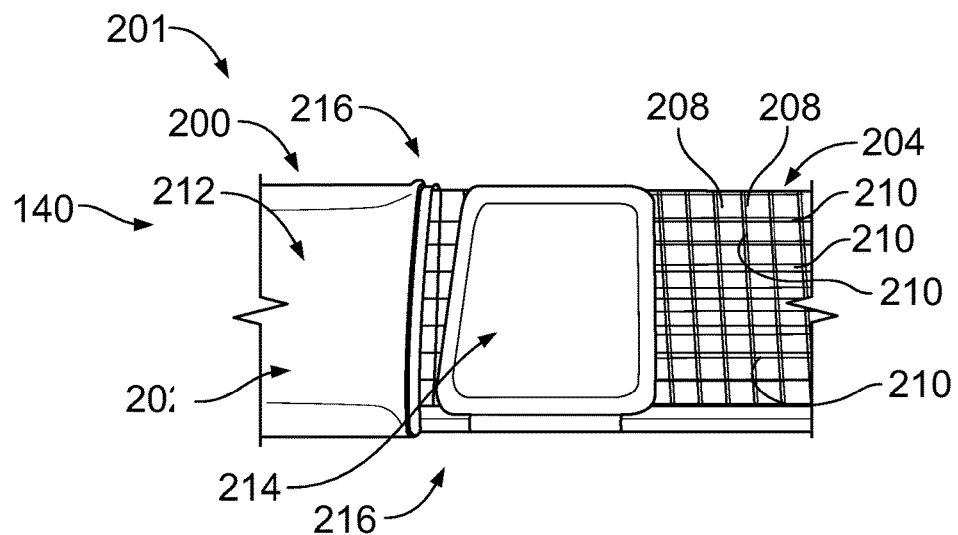
FIG. 17 illustrates an end view of a braid attachment of a UV lamp, according to an embodiment of the present disclosure.

FIG. 17 illustrates an end view of a braid attachment 200 of a UV lamp 140, according to an embodiment of the present disclosure. The UV lamp 140 includes or otherwise couples to the braid attachment 200. The UV lamp 140 may be part of a portable sanitizing system, such as that shown and described with respect to FIGS. 1-15, or a fixed sanitizing system.

In at least one embodiment, the braid attachment 200 is an electrical braid at an end 202 of the UV lamp 140. For example, the braid attachment 200 is configured to electrically connect to an electrical source, such as through one or more of an electrical braid, wires, couplings, or the like. The braid attachment 200 may extend along a length of the UV lamp 140. For example, the braid attachment 200 may provide a cage structure that extends along at least a portion of a length of the UV lamp 140.

The braid attachment 200 includes a mesh or screen 204 including a plurality of longitudinal linear wires 206 that intersect with a plurality of lateral linear wires 208. For example, the longitudinal linear wires 206 may orthogonally intersect the lateral linear wires 208, thereby forming a plurality of grid members 210. In this manner, the longitudinal linear wires 206 and the lateral linear wires 208 may provide grid lines. The longitudinal linear wires 206 and the lateral linear wires 208 may be formed from a metal, for example.

In at least one embodiment, tape 212 is wrapped around the end 202 of the UV lamp 140. The tape 212 may extend around at least a portion of an end of the braid attachment 200. The tape 212 could be made of materials such as polyimide (Kapton), PEEK, Teflon, or Fiberglass. For example, in at least one embodiment, the tape 212 is or includes a fiberglass wrap that is wrapped around the portion of the braid attachment 200. The tape 212 can be wrapped around a compression area to secure the conductive layer and braid attachment 200.

A foil 214 is secured around the braid attachment 200 at a compression area 216. At least a portion of the foil 214 may be inboard from the tape 212. That is, the foil 214 may be between the tape 212 and a center of the braid attachment 200. Optionally, the tape 212 may wrap around an entirety of the foil 214, thereby compressing the foil 214 into the braid attachment 200. The foil 214 provides a greater area of electrical contact (such as in relation to an electrical coupling, such an electrical braid) and spreads heat thereover to prevent a thermal hotspot.

The foil 214 wraps around at least a portion of the braid attachment 200. In at least one embodiment, the tape 212 is wrapped around at least a portion of the foil 214 (which provides a conductive layer) to compress the foil 214 in relation to the braid attachment 200. That is, the wrapped tape 212 compresses the foil 214 into the braid attachment 200.

In at least one other embodiment, the foil 214 does not touch the tape 212. For example, the tape 212 may not wrap around the foil 214. Optionally, the tape 212 may not be used. Instead, a clamp may be used to compress the foil 214 in relation to the braid attachment 200. In at least one other embodiment, both the tape 212 and the clamp may be used to compress the foil 214 in relation to the braid attachment 200.

In at least one embodiment, the foil 214 is formed of copper. As another example, the foil 214 is formed of aluminum. The foil 214 provides a thin conductive layer that wraps around at least a portion of the braid attachment 200. As an example, the foil 214 may have a thickness of 5 millimeters or less.

Figure 18:
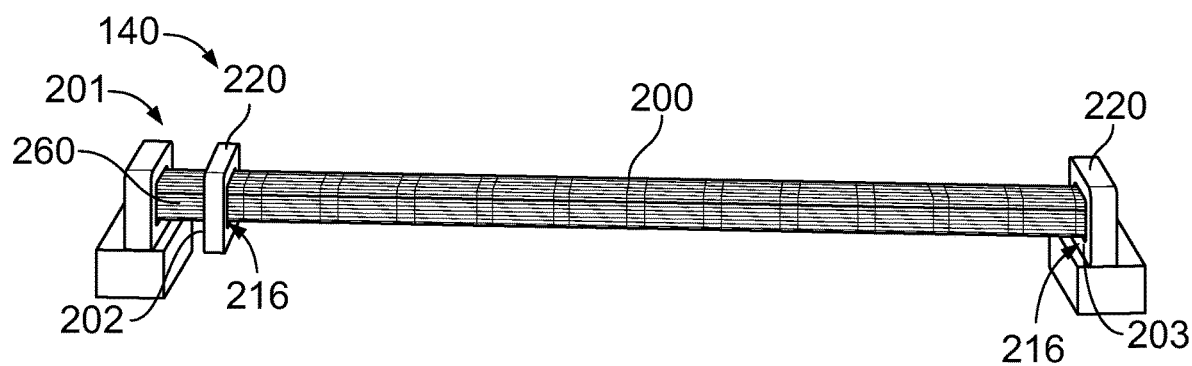
FIG. 18 illustrates a lateral view of a UV lamp, according to an embodiment of the present disclosure.

FIG. 18 illustrates a lateral view of the UV lamp 140, according to an embodiment of the present disclosure. The UV lamp 140 includes (or otherwise couples to) the braid attachment 200 extending between ends 202 and 203. Compression areas 216 are located at or proximate to the ends 202 and 203. Referring to FIGS. 17 and 18, the foil 214 providing the conductive layer (that is, the foil 214 is the conductive layer) is first secured to at least a portion of the braid attachment 200. After the foil 214 is secured to the braid attachment 200 at the compression area 216, a clamp 220 is secured to the foil 214, thereby exerting a clamping force into the foil 214 at the compression area 216.

In at least one embodiment, the clamp 220 is formed of plastic. For example, the clamp may be formed of a thermoplastic material, and may have a C or U shape, with a hook on an open side to attach the open ends together to provide additional clamping force.

Figure 19:
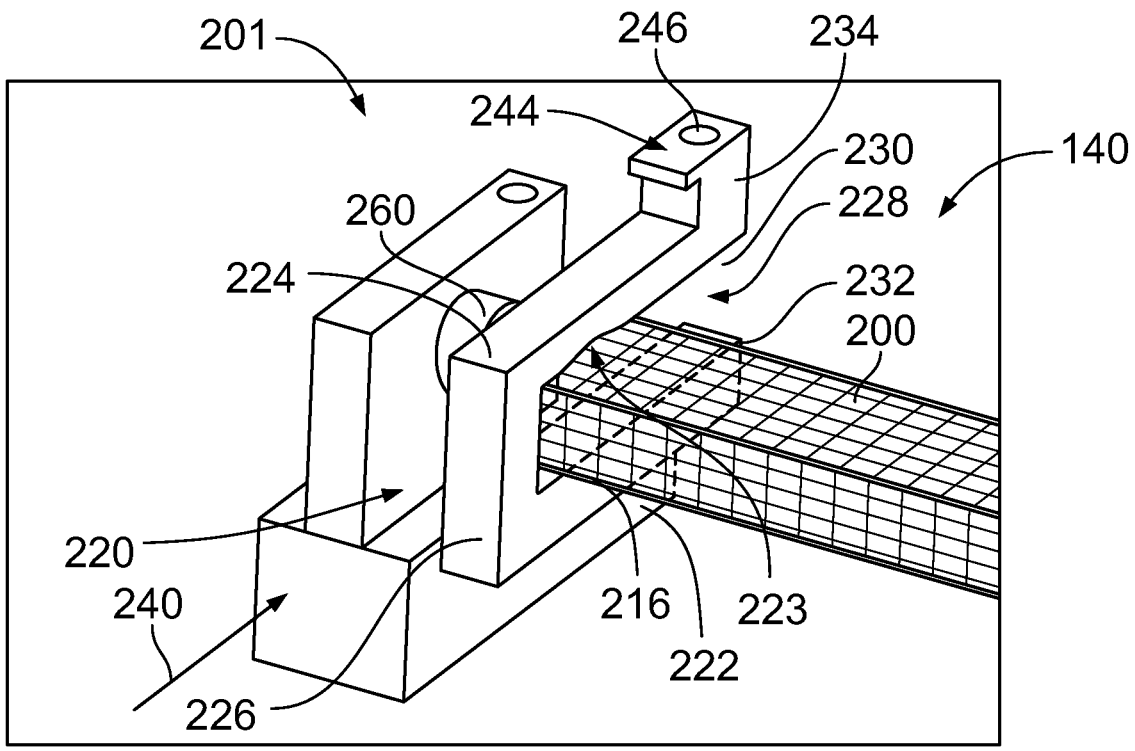
FIG. 19 illustrates a perspective end view of the braid attachment of the UV lamp having a clamp, according to an embodiment of the present disclosure.

FIG. 19 illustrates a perspective end view of the braid attachment 200 of the UV lamp 140 having the clamp 220, according to an embodiment of the present disclosure.

The clamp 220 includes a first arm 222 spaced apart from a second arm 224 by an orthogonal extension beam 226. A clamping channel 228 is defined between the first arm 222, the second arm 224 and the extension beam 226. An opening 230 that leads into the clamping channel 228 is defined between free ends 232 and 234 of the first arm 222 and the second arm 224, respectively. As such, the clamp 220 has a C or U shape.

After the foil 214 (shown in FIG. 16) is wrapped around the compression area 216 of the braid attachment 200, the clamp 220 is moved over the compression area 216 in the direction of arrow 240, such that the compression area 216 of the braid attachment 200 is sandwiched between first arm 222 and the second arm 224. In at least one embodiment, the first arm 222 and/or the second arm 224 includes a fastener coupling 244, such as a protuberance, that includes a passage 246 for receiving a fastener, such as a screw or bolt. The fastener is secured within the passage 246 and connects to the opposite first or second arm 222 or 224 that overhang the compression area 216. The fastener may then be tightened, thereby urging the first arm 222 and the second arm 224 toward one another, which increases the clamping force of the clamp 220.

In at least one embodiment, the foil 214 can be applied to a portion of the clamp 220. For example, tape 223 secured to interior surfaces of the arm 222 or 224 may include the foil 214. As an example, the tape 223 can be a 1 inch by 0.5 inch copper tape applied over the braid attachment 200 and/or to the interior portion of the clamp 220.

The clamp 220 is placed on the compression area 216. The clamp 220 mechanically secures the conductive layer (for example, the foil 214) to at least a portion of the electrical braid (for example, the braid attachment 200).

Figure 20:
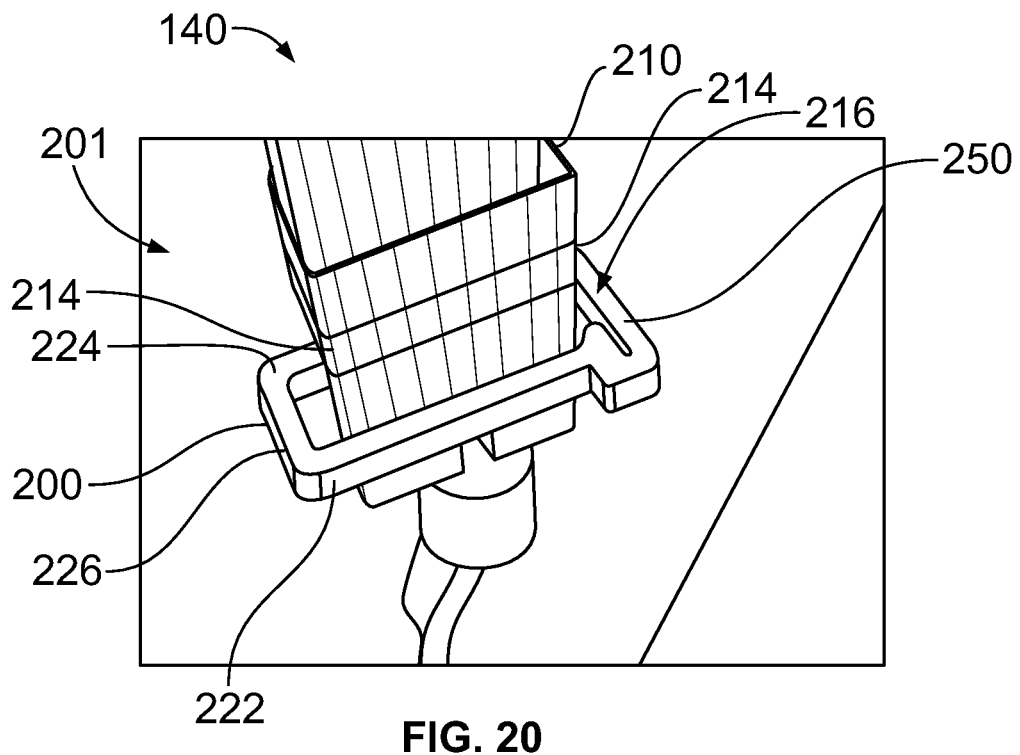
FIG. 20 illustrates a perspective end view of the clamp secured around a conductive layer wrapped around a compressive area of the braid attachment, according to an embodiment of the present disclosure.

FIG. 20 illustrates a perspective end view of the clamp 220 secured around the conductive layer (that is, the foil 214) wrapped around the compressive area 216 of the braid attachment 200, according to an embodiment of the present disclosure. In this embodiment, a securing arm 250 may extend from one or the other of the first arm 222 or the second arm 224 opposite from the extension beam 226. The securing arm 250 may selectively lock and unlock the first arm 222 to the second arm 224, thereby ensuring that the clamp 220 exerts a uniform and consistent clamping force. A fastener may or may not be used to secure the securing arm 250 in position. In at least one embodiment, the securing arm 250 latches or snaps in position with or without the use of a separate fastener.

Referring to FIGS. 17-20, certain embodiments of the present disclosure provide a method to maintain an electrical connection and contact on the UV lamp 140, such as a 222 nm excimer lamp. The method includes applying a thin conductive layer (such as the foil 214) at the compression area 216 where an electrical coupling 260 (such as an electrical braid) contacts the UV lamp 140. The method also includes compressing the conductive layer and the electrical connection 260 to the compression area 216 with a mechanical restraining device such as tape 212 and/or the clamp 220. The tape 212 and/or the clamp 220 are formed of materials that maintain structural and thermal capabilities at a temperature of at least 200 degrees C., for example. In at least one embodiment, the tape 212 is used in relation to the foil 214 without the clamp 220. In at least one other embodiment, both the tape 212 and the clamp 220 are used in relation to the foil 214. In at least one other embodiment, the clamp 220 is used in relation to the foil 214 without the tape 212.

Certain embodiments of the present disclosure provide a system 201 for connecting the UV lamp 140 with the electrical coupling 260. The system 201 includes the braid attachment 200 coupled to the UV lamp 140 For example, the UV lamp 140 may include the braid attachment 200. Optionally, the braid attachment 200 may be separately coupled to the UV lamp 140. A conductive layer (such as the foil 214) is secured to at least a portion (such as an end portion) of the braid attachment 200. In at least on embodiment, the conductive layer includes the foil 214 wrapped around the at least a portion of the braid attachment 200.

In at least on embodiment, the system 201 also includes a mechanical restraining device configured to secure the braid attachment 200 to the electrical coupling 260. For example, the mechanical restraining device includes the tape 212 wrapped around one or both of the portion of the braid attachment 200 or at least a portion of the conductive layer. As another example, the mechanical restraining device includes the clamp 220 secured around one or both of the portion of the braid attachment 200 or at least a portion of the conductive layer. As another example, the mechanical restraining device includes the tape 212 wrapped around one or both of the portion of the braid attachment 200 or at least a portion of the conductive layer, and the clamp 220 secured around one or both of the portion of the braid attachment 200 or at least a portion of the conductive layer.

Figure 21:
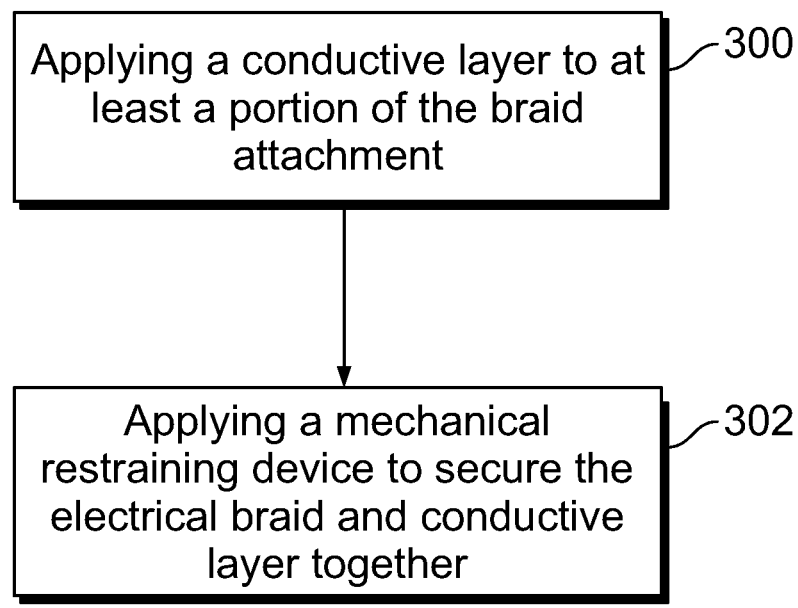
FIG. 21 illustrates a flow chart of a method of securing an electrical coupling to a portion of a UV lamp, according to an embodiment of the present disclosure.

FIG. 21 illustrates a flow chart of a method of securing the electrical coupling 260 (such as one or an electrical braid, one more electrical wires, fixtures, and/or the like that connect to a source of power) to a portion of the UV lamp, according to an embodiment of the present disclosure. The UV lamp may include the braid attachment 200, or the braid attachment 200 may be separately coupled to the UV lamp.

In at least one embodiment, the method includes applying, at 300, a conductive layer (such as the foil 214) to at least a portion of the braid attachment (such as the braid attachment 200) to provide a greater area of electrical contact and spread heat to prevent a thermal hotspot. Next, in at least one embodiment, the method includes applying, at 302, a mechanical restraining device (such as the tape 212 and/or the clamp 220) to secure the electrical braid and conductive layer together. The mechanical restraining device may be applied around at least a portion of the conductive layer.

Figure 22:
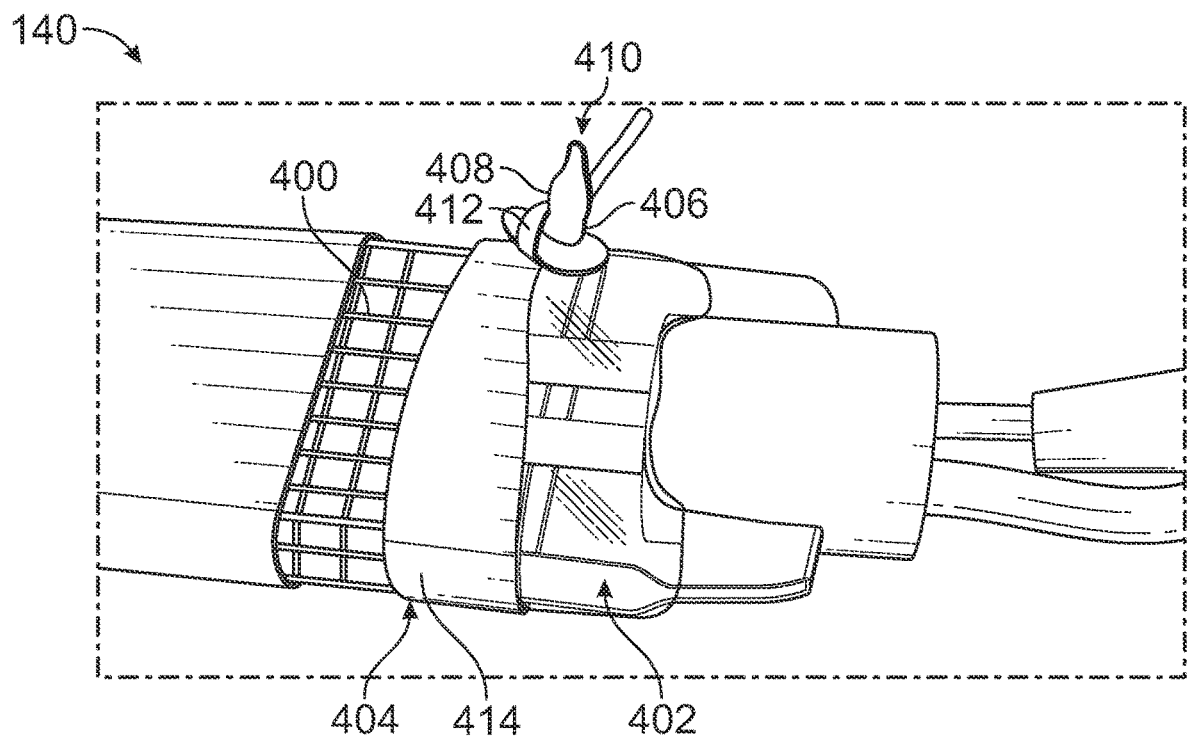
FIG. 22 illustrates an end view of a braid attachment of a UV lamp, according to an embodiment of the present disclosure.

FIG. 22 illustrates an end view of a braid attachment 400 of a UV lamp 140, according to an embodiment of the present disclosure. In at least one embodiment, a compressive wrap, such as a fiberglass wrap 402, is wrapped around the portion 404 of the braid attachment 400. The fiberglass wrap 402 is first wrapped around the portion 404 of the braid attachment 400. Ends 406 and 408 of the fiberglass wrap 402 are tied together in a knot 410. At least a portion of the fiberglass wrap 402 is bonded with an epoxy 412. For example, the knot 410 is bonded by an epoxy 412, which may be cured at a temperature of 350 degrees F.

In at least one embodiment, the knot 410 including the epoxy 412 is spaced apart from the braid attachment 400, such as by wrapped layers 414 of the fiberglass wrap 402. That is, the wrapped layers 414 separate the knot 410, which is bonded by the epoxy 412, from the braid attachment 400 or other heat-generating portions of the UV lamp 140. As such, the epoxy 412 is not directly subjected to high temperatures generated by the UV lamp 140. Instead, the wrapped layers 414 provide a heat-dissipating buffer between the knot 410 and the braid attachment 400. Accordingly, the epoxy 412 and the knot 410 may generally be below 200 degrees C. when the UV lamp 140 is activated.

In at least one embodiment, a thermoset, such as a Bismaleimide/cyanate ester composite resin thermoset may be used in place of, or in addition to, the epoxy 412. The thermoset is able to withstand temperatures that exceed 200 degrees C.

Figure 23:
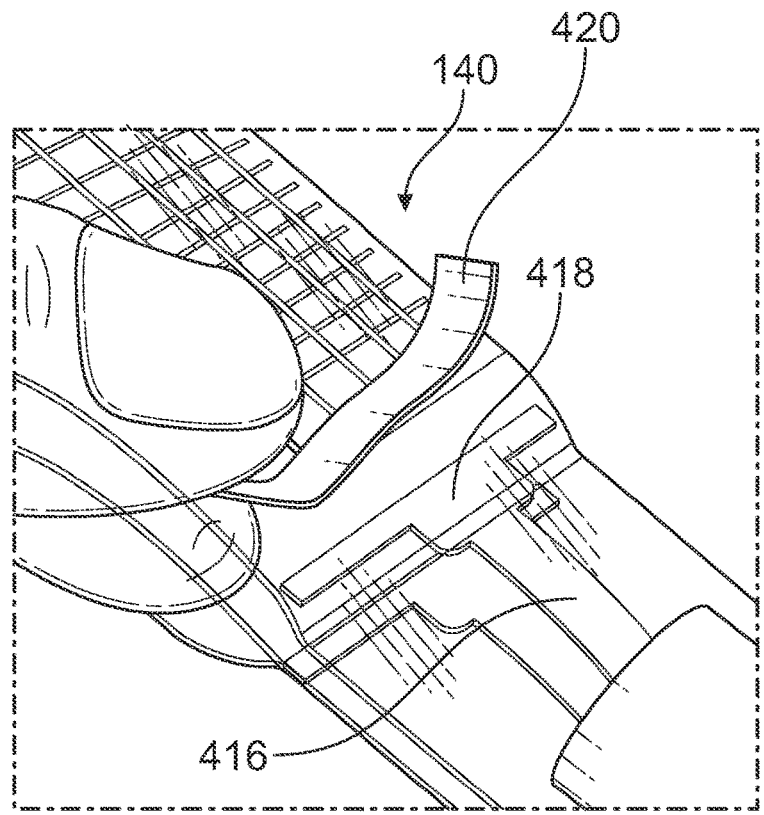
FIG. 23 illustrates a perspective top view of a braid attachment of a UV lamp, according to an embodiment of the present disclosure.

FIG. 23 illustrates a perspective top view of the braid attachment 400 of the UV lamp 140. A connecting electrical braid 416 connects to the braid attachment 400. A mechanical restraining device or constraint, such as a fiberglass wrap, compressively secures at least a portion of the connecting electrical braid 416 to the braid attachment 400.

In at least one embodiment, a conductive layer 420, such as copper or aluminum foil, is secured over and end 418 of the connecting electrical braid 416 and the braid attachment 400.

Figure 24:
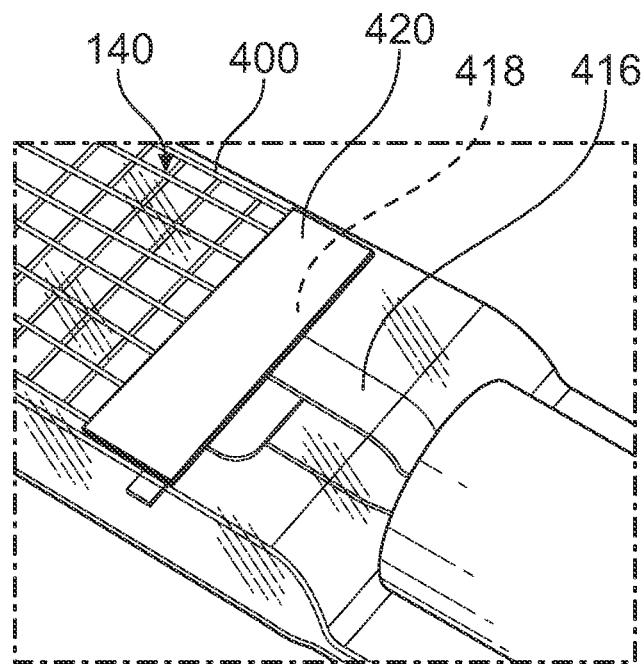
FIG. 24 illustrates a perspective top view of a conductive foil secured over a portion of the braid attachment and a connecting electrical braid, according to an embodiment of the present disclosure.
Figure 25:
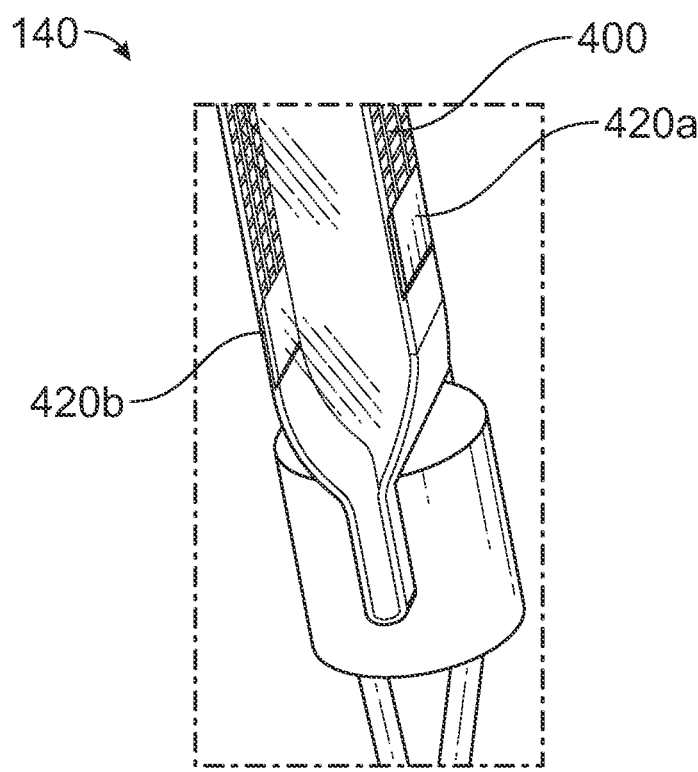
FIG. 25 illustrates a lateral view of the braid attachment of the UV lamp, according to an embodiment of the present disclosure.

FIG. 24 illustrates a perspective top view of the conductive foil 420 secured over the portion of the braid attachment 400 and the connecting electrical braid 416. FIG. 25 illustrates a lateral view of the braid attachment 400 of the UV lamp 140. The conductive foil 420 may be positioned on opposite sides or surfaces of the braid attachment 400. In at least one embodiment, the conductive foil 420 on the opposite surfaces may not connect together. Instead, a first conductive foil 420a is on one side or surface, and a second conductive foil 420b is on an opposite side or surface.

Figure 26:
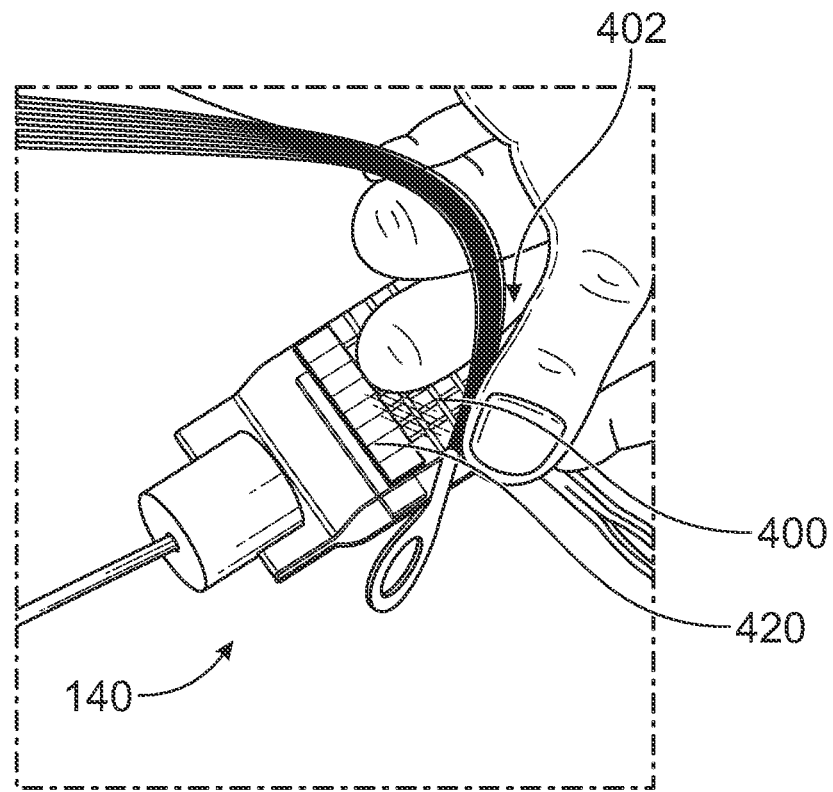
FIG. 26 illustrates a perspective view of a fiberglass wrap being wrapped around the portion of the braid attachment, according to an embodiment of the present disclosure.

FIG. 26 illustrates a perspective view of the fiberglass wrap 402 being wrapped around the portion of the braid attachment 400. The fiberglass wrap 402 may be wrapped around the conductive foil 420 and the portion of the braid attachment 400.

Figure 27:
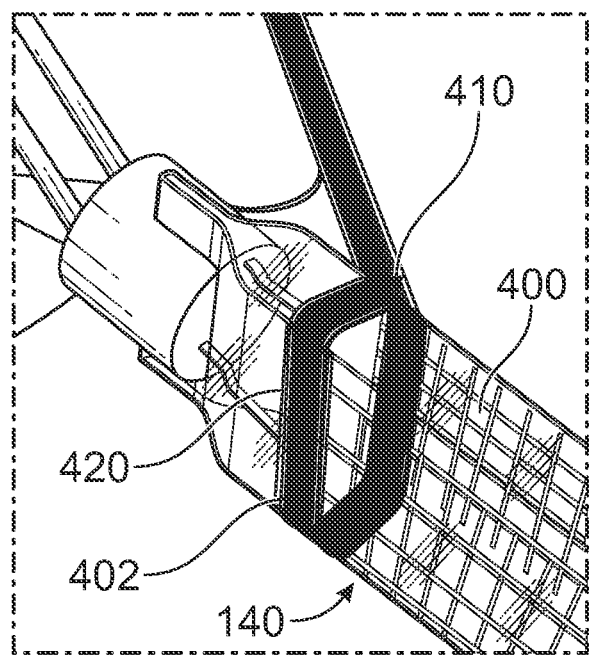
FIG. 27 illustrates a perspective view of ends of the fiberglass wrap being tied together in a knot, according to an embodiment of the present disclosure.
Figure 28:
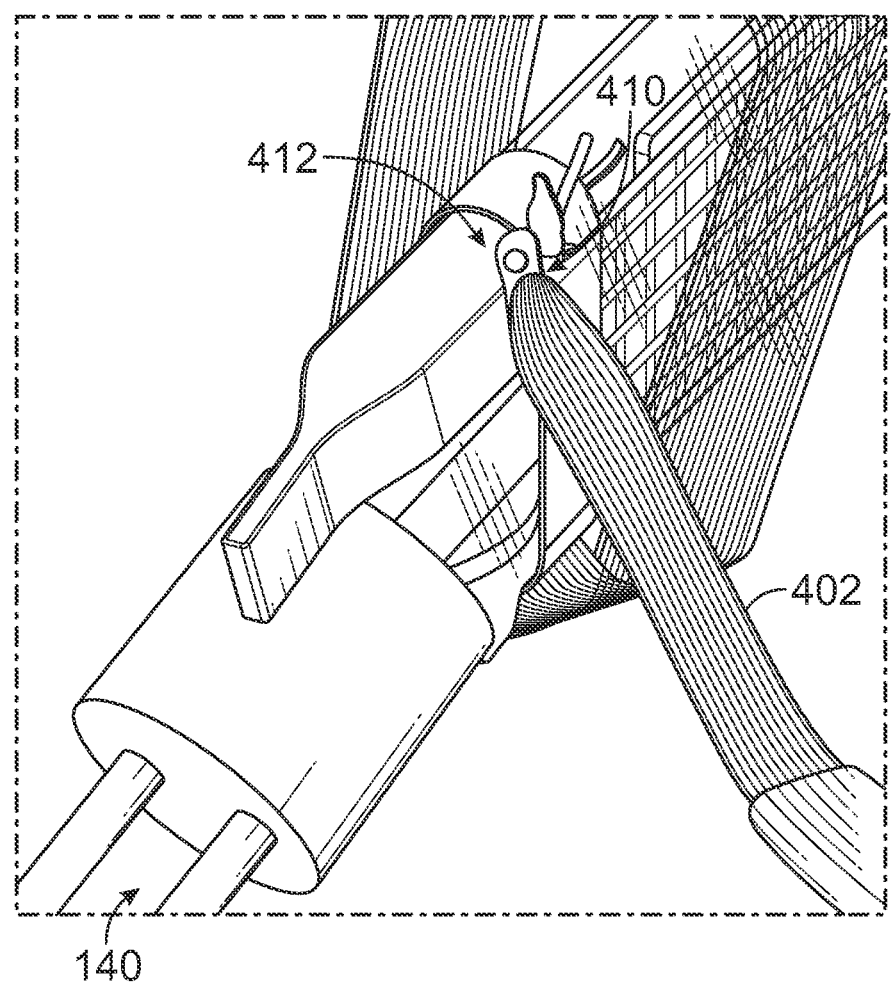
FIG. 28 illustrates a perspective view of an epoxy applied to the knot, according to an embodiment of the present disclosure.

FIG. 27 illustrates a perspective view of ends of the fiberglass wrap 402 being tied together in the knot 410. FIG. 28 illustrates a perspective view of the epoxy 412 applied to the knot 410. The epoxy 412 is an adhesive that bonds the knot 410. As an example, the epoxy 412 is a high temperature adhesive that is configured to maintain an effective bond at temperatures that exceed 350 degrees F. As a non-limiting example, the epoxy 412 may be Loctite 9394.

Figure 29:
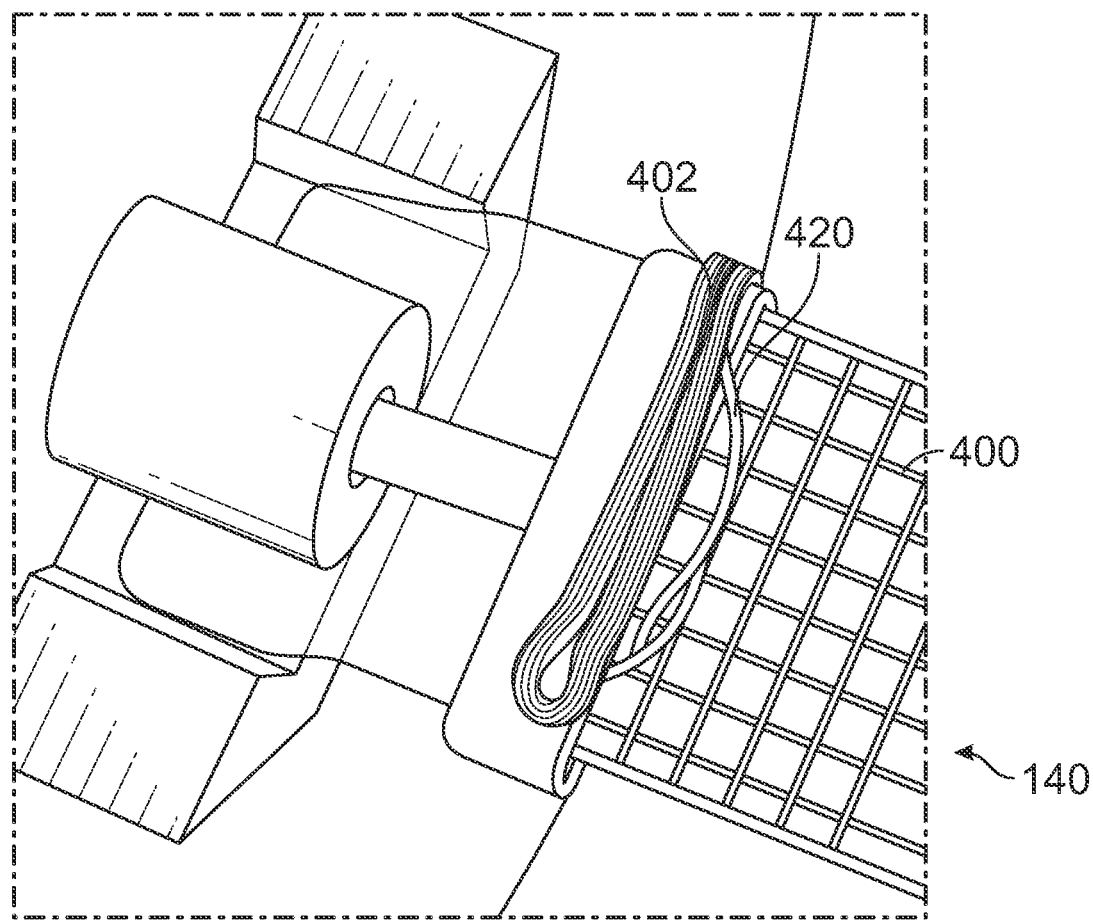
FIG. 29 illustrates a perspective view of the fiberglass wrap secured around the portion of the braid attachment, according to an embodiment of the present disclosure.

FIG. 29 illustrates a perspective view of the fiberglass wrap 402 secured around the portion of the braid attachment 400. The fiberglass wrap 402 compresses the conductive foil 420, the portion of the braid attachment 400, and the end of the connecting electrical braid 416 together, thereby providing a secure and reliable electrical connection.

Figure 30:
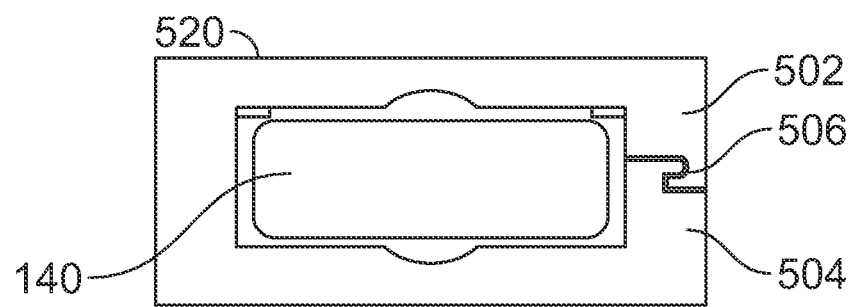
FIG. 30 illustrates a schematic diagram of a clamp secured around a portion of a UV lamp, according to an embodiment of the present disclosure.

FIG. 30 illustrates a schematic diagram of a clamp 500 secured around a portion of a UV lamp 140, according to an embodiment of the present disclosure. The clamp 500 is secured around a portion of the UV lamp, such as the braid attachment 400, as shown in FIG. 22, for example. Referring to FIGS. 22-30, the clamp 500 may be secured over the fiberglass wrap 402. Optionally, the clamp 500 may be used in place of the fiberglass wrap 402.

The clamp 500 may be formed of a plastic or thermoplastic material. The clamp 500 includes ends 502 and 504 that may cooperate to secure together, such as through a latch, snap, or other such connection 506. The clamp 500 may be a clip that is securely clamps around the portion of the UV lamp 140.

Figure 31:
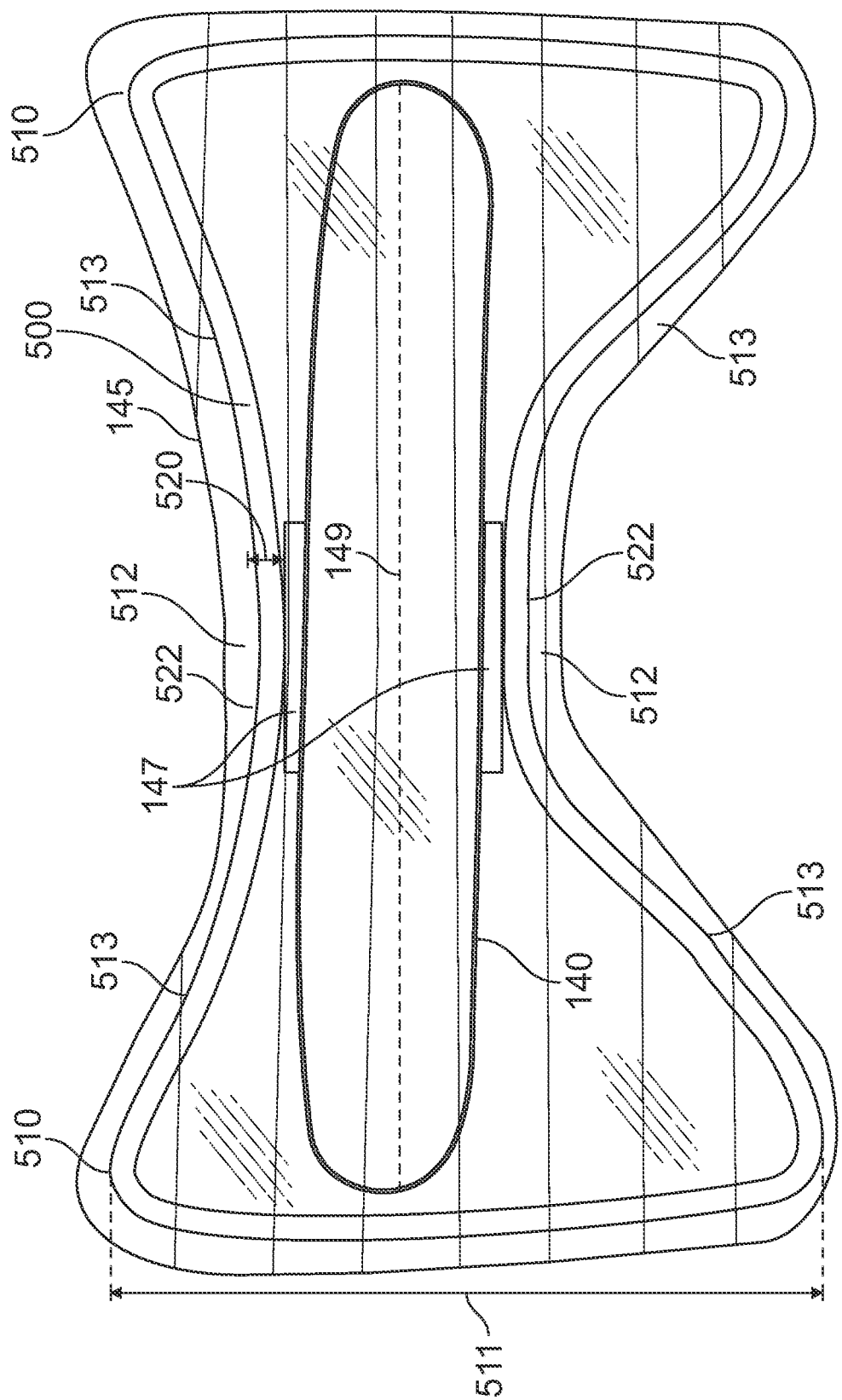
FIG. 31 illustrates an axial cross-sectional view of the clamp secured around the portion of the UV lamp, according to an embodiment of the present disclosure.

FIG. 31 illustrates an axial cross-sectional view of the clamp 500 secured around the portion of the UV lamp 140, according to an embodiment of the present disclosure. In at least one embodiment, the clamp 500 is formed of a resilient material, such as a plastic, that is configured to exert a compressive force into the portion of the UV lamp 140, thereby securing an electrical connection therein.

The UV lamp 140 includes a bulb 145 connected to electrodes 147. The clamp 500 may be secured around at least portions of the bulb 145 and the electrodes 147.

In at least one embodiment, the clamp 500 includes expanded ends 510 connected together by a recessed connecting beam 512. The expanded ends 510 have a greater height 511 than the recessed connecting beam 512. The expanded ends 510 may connect to the recessed connecting beam 512 through smooth, curved transitions 513.

A thickness 520 of the clamp 500 may vary around a perimeter. The varying thickness is configured to provide a desired stiffness and/or compressive force. For example, a thickness 520 of the recessed connecting beam 512 may be greater than a thickness of the expanded ends 510. Optionally, the thickness 520 of the clamp 500 may be uniform throughout.

As shown, the recessed connecting beam 512 inwardly curves towards the UV lamp 140, thereby forming inwardly-curved segments 522. The inwardly-curved segments 522 curve towards one another and a central plane 149 of the UV lamp 140. The inward curved of the recessed connecting beam 512 allows for a high preload and low spring rate, thereby mitigating differences in thermal expansion between the UV lamp 140 and the clamp 500.

Alternatively, the clamp 500 may be sized and shaped differently than shown. For example, the clamp 500 may include a rectangular outer cross-section.

In at least one other embodiment, in addition to (or in place of) the clamp 500, a resilient band may be used. For example, an elastomeric band may be used in addition to, or in place of, the clamp 500.

Figure 32:
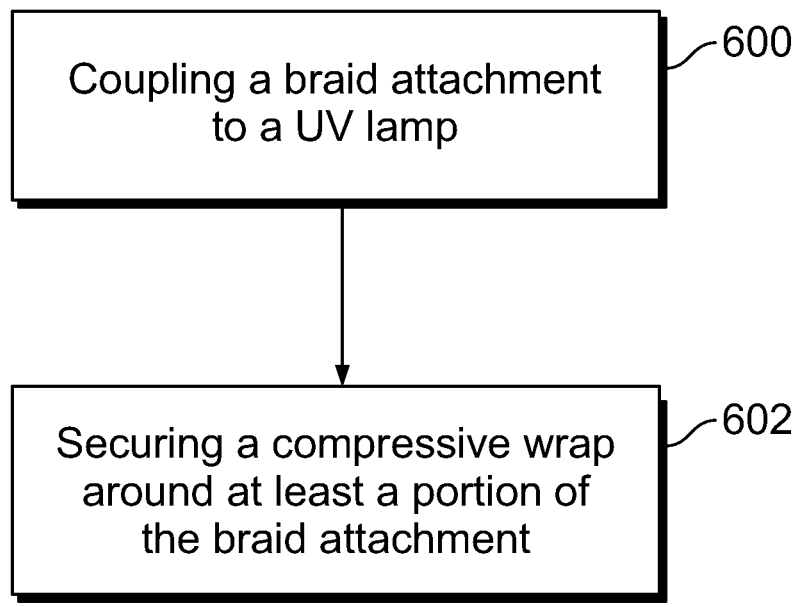
FIG. 32 illustrates a flow chart of a method for connecting an ultraviolet (UV) lamp with an electrical coupling, according to an embodiment of the present disclosure.

FIG. 32 illustrates a flow chart of a method for connecting an ultraviolet (UV) lamp with an electrical coupling, according to an embodiment of the present disclosure. The method includes coupling (600) a braid attachment to a UV lamp, and securing (602) a compressive wrap around at least a portion of the braid attachment. In at least one embodiment, the method includes forming the compressive wrap from fiberglass.

In at least one embodiment, the method includes securing a conductive layer to the at least a portion of the braid attachment. Said securing the compressive wrap may include securing the compressive wrap around at least a portion of the conductive layer.

In at least one embodiment, said securing (602) includes tying ends of the compressive wrap together in a knot. Said securing (602) may also include bonding the knot with an epoxy. Said securing (602) may also include separating the knot from the at least a portion of the braid attachment by wrapped layers of the compressive wrap.

In at least one embodiment, the method also includes securing a clamp around one or both of the at least a portion of the braid attachment or at least a portion of the compressive wrap.

Figure 33:
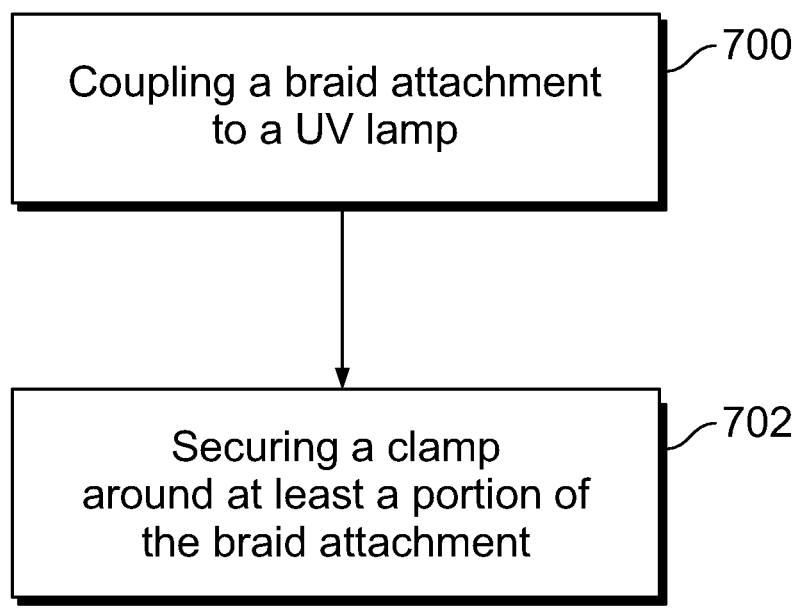
FIG. 33 illustrates a flow chart of a method for connecting an ultraviolet (UV) lamp with an electrical coupling, according to an embodiment of the present disclosure.

FIG. 33 illustrates a flow chart of a method for connecting an ultraviolet (UV) lamp with an electrical coupling, according to an embodiment of the present disclosure. The method includes coupling (700) a braid attachment to a UV lamp, and securing (702) a clamp around at least a portion of the braid attachment. In at least one embodiment, the method also includes securing a conductive layer to the at least a portion of the braid attachment. Said securing (702) further includes securing the clamp around at least a portion of the conductive layer.

Further, the disclosure comprises embodiments according to the following clauses:

Clause 1. A system for connecting an ultraviolet (UV) lamp with an electrical coupling, the system comprising:
a braid attachment of the UV lamp; and
a compressive wrap secured around at least a portion of the braid attachment.

Clause 2. The system of Clause 1, wherein the compressive wrap is formed of fiberglass.

Clause 3. The system of Clauses 1 or 2, further comprising a conductive layer secured to the at least a portion of the braid attachment, wherein the compressive wrap is secured around at least a portion of the conductive layer.

Clause 4. The system of Clause 3, wherein the conductive layer comprises a foil.

Clause 5. The system of any of Clauses 1-5, wherein the compressive wrap comprises ends tied together in a knot.

Clause 6. The system of Clause 5, further comprising an epoxy that bonds the knot.

Clause 7. The system of Clauses 5 or 6, wherein the knot is separated from the at least a portion of the braid attachment by wrapped layers of the compressive wrap.

Clause 8. The system of any of Clauses 1-7, further comprising a clamp secured around one or both of the at least a portion of the braid attachment or at least a portion of the compressive wrap.

Clause 9. The system of Clause, wherein the clamp is formed of a plastic.

Clause 10. The system of Clauses 8 or 9, wherein the clamp comprises expanded ends connected together by a recessed connecting beam.

Clause 11. The system of Clause 10, wherein the recessed connecting beam inwardly curves toward the UV lamp.

Clause 12. The system of any of Clauses 8-11, wherein a thickness of the clamp varies around a perimeter.

Clause 13. A method for connecting an ultraviolet (UV) lamp with an electrical coupling, the method comprising:
coupling a braid attachment to a UV lamp; and
securing a compressive wrap around at least a portion of the braid attachment.

Clause 14. The method of Clause 13, further comprising forming the compressive wrap from fiberglass.

Clause 15. The method of Clauses 13 or 14, further comprising securing a conductive layer to the at least a portion of the braid attachment, wherein said securing the compressive wrap comprises securing the compressive wrap around at least a portion of the conductive layer.

Clause 16. The method of any of Clauses 13-15, wherein said securing comprises tying ends of the compressive wrap together in a knot.

Clause 17. The method of any of Clause 16, wherein said securing further comprises bonding the knot with an epoxy.

Clause 18. The method of Clauses 16 or 17, wherein said securing further comprises separating the knot from the at least a portion of the braid attachment by wrapped layers of the compressive wrap.

Clause 19. The method of any of Clauses 13-18, further comprising securing a clamp around one or both of the at least a portion of the braid attachment or at least a portion of the compressive wrap.

Clause 20. The method of Clause 19, wherein the clamp comprises expanded ends connected together by a recessed connecting beam.

Clause 21. The method of Clause 20, wherein the recessed connecting beam inwardly curves toward the UV lamp.

Clause 22. The method of any of Clauses 19-21, further comprises varying a thickness of the clamp around a perimeter.

Clause 23. A system for connecting an ultraviolet (UV) lamp with an electrical coupling, the system comprising:
a braid attachment of the UV lamp; and
a clamp secured around at least a portion of the braid attachment.

Clause 24. The system of Clause 23, further comprising a conductive layer secured to the at least a portion of the braid attachment, wherein the clamp is secured around at least a portion of the conductive layer.

Clause 25. The system of Clause 24, wherein the conductive layer comprises a foil.

Clause 26. The system of Clauses 24 or 25, wherein the clamp is formed of a plastic.

Clause 27. The system of any of Clauses 24-26, wherein the clamp comprises expanded ends connected together by a recessed connecting beam.

Clause 28. The system of Clause 27, wherein the recessed connecting beam inwardly curves toward the UV lamp.

Clause 29. The system of any of Clauses 23-28, wherein a thickness of the clamp varies around a perimeter.

Clause 30. A method for connecting an ultraviolet (UV) lamp with an electrical coupling, the method comprising:
coupling a braid attachment to a UV lamp; and
securing a clamp around at least a portion of the braid attachment.

Clause 31. The method of Clause 30, further comprising securing a conductive layer to the at least a portion of the braid attachment, wherein said securing the clamp comprises securing the clamp around at least a portion of the conductive layer.

As described herein, embodiments of the present disclosure provide systems and a methods for maintaining a reliable connection between a UV lamp an electrical coupling.

While various spatial and directional terms, such as top, bottom, lower, mid, lateral, horizontal, vertical, front and the like can be used to describe embodiments of the present disclosure, it is understood that such terms are merely used with respect to the orientations shown in the drawings. The orientations can be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) can be used in combination with each other. In addition, many modifications can be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims and the detailed description herein, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and can include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A system comprising:
   an ultraviolet (UV) lamp;
   a braid attachment extending along one or more portions of a length of the UV lamp;
   a compressive wrap secured around a portion of the braid attachment; and
   a clamp secured around one or both of the portion of the braid attachment or one or more portions of the compressive wrap, wherein the clamp comprises expanded ends connected together by a recessed connecting beam.

2. The system of claim 1, wherein the compressive wrap is formed of fiberglass.

3. The system of claim 1, further comprising a conductive layer secured to the portion of the braid attachment, wherein the compressive wrap is secured around one or more portions of the conductive layer.

4. The system of claim 3, wherein the conductive layer comprises a foil.

5. The system of claim 1, wherein the compressive wrap comprises ends tied together in a knot.

6. The system of claim 5, further comprising an epoxy that bonds the knot.

7. The system of claim 5, wherein the knot is separated from the portion of the braid attachment by wrapped layers of the compressive wrap.

8. The system of claim 1, wherein the clamp is formed of a plastic.

9. The system of claim 1, wherein the recessed connecting beam inwardly curves toward the UV lamp.

10. The system of claim 1, wherein a thickness of the clamp varies around a perimeter.

11. The system of claim 1, wherein the braid attachment includes a cage structure.

12. A system comprising:
    an ultraviolet (UV) lamp;
    a braid attachment extending along one or more portions of the UV lamp; and
    a clamp secured around a portion of the braid attachment, wherein the clamp comprises expanded ends connected together by a recessed connecting beam.

13. A method comprising:
    extending a braid attachment along one or more portions of an ultraviolet (UV) lamp;
    securing a compressive wrap around a portion of the braid attachment; and
    securing a clamp around one or both of the portion of the braid attachment or one or more portions of the compressive wrap, the clamp comprises expanded ends connected together by a recessed connecting beam, the recessed connecting beam inwardly curves toward the UV lamp, and further comprising varying a thickness of the clamp around a perimeter.

14. The method of claim 13, further comprising forming the compressive wrap from fiberglass.

15. The method of claim 13, further comprising securing a conductive layer to the portion of the braid attachment, wherein said securing the compressive wrap comprises securing the compressive wrap around one or more portions of the conductive layer.

16. The method of claim 13, wherein said securing the compressive wrap comprises tying ends of the compressive wrap together in a knot, wherein said securing further comprises bonding the knot with an epoxy.

17. The method of claim 16, wherein said securing the compressive wrap comprises separating the knot from the portion of the braid attachment by wrapped layers of the compressive wrap.

18. The system of claim 12, wherein the clamp is formed of a plastic.

19. A method comprising:
    extending a braid attachment along one or more portions of an ultraviolet (UV) lamp; and
    securing a clamp around a portion of the braid attachment, wherein the clamp comprises expanded ends connected together by a recessed connecting beam.

20. The system of claim 12, wherein the recessed connecting beam inwardly curves toward the UV lamp.

21. The system of claim 12, wherein a thickness of the clamp varies around a perimeter.

* * * * *